US012714392B2

(12) United States Patent
Agarwal et al.

(10) Patent No.: US 12,714,392 B2
(45) Date of Patent: Aug. 25, 2026

(54) SYSTEM AND METHOD FOR TRANSESOPHAGEAL ECHOCARDIOGRAM-GUIDED IMPLANTATION OF A VALVE DEVICE

(71) Applicant: Anumana, Inc., Cambridge, MA (US)

(72) Inventors: Animesh Agarwal, San Mateo, CA (US); Suthirth Vaidya, Bengaluru (IN); Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 19/047,323

(22) Filed: Feb. 6, 2025

(65) Prior Publication Data

US 2026/0096880 A1 Apr. 9, 2026

Related U.S. Application Data

(60) Provisional application No. 63/705,376, filed on Oct. 9, 2024.

(51) Int. Cl.
*A61F 2/24* (2006.01)
*A61B 8/00* (2006.01)
(Continued)

(52) U.S. Cl.
CPC .......... *A61F 2/2427* (2013.01); *A61B 8/0883* (2013.01); *A61B 8/12* (2013.01);
(Continued)

(58) Field of Classification Search
CPC ... A61B 8/12; A61B 2034/102; A61B 8/0883; A61F 2/2427; G16H 30/40; G16H 30/50; G06T 7/60; G06T 7/62; G06T 7/0012
See application file for complete search history.

(56) References Cited

U.S. PATENT DOCUMENTS 7,780,599 B2 8/2010 Nierich
8,172,757 B2 5/2012 Jaffe et al.
(Continued)

FOREIGN PATENT DOCUMENTS

CN 105931549 A 9/2016
CN 114831729 A 5/2024
(Continued)

OTHER PUBLICATIONS

N.C Nanda et al.Simulation for transthoracic echocardiography of aortic valve Ann Card Anaesth. Jul.-Sep. 2016;19(3):498-504.
(Continued)

*Primary Examiner* — John D Li
(74) *Attorney, Agent, or Firm* — CALDWELL LLC

(57) ABSTRACT

A system for transesophageal echocardiogram-guided implantation of a valve device, the system including at least a transesophageal echocardiogram system configured to detect at least an ultrasound image and at least a computing device configured to receive at least an ultrasound image, generate at least a 3D cardiac model representative of a heart of the patient as a function of at least an ultrasound image wherein the at least an ultrasound image includes a two-dimensional image of the heart of the patient and wherein the 3D cardiac model includes a three dimensional interpolation of the two-dimensional image, determine a valve model datum as a function of the 3D cardiac model, receive at least valve model representative of at least a cardiovascular device to be placed within the patient as a function of the valve model datum and display the at least a 3D cardiac model and at least a valve model.

22 Claims, 13 Drawing Sheets

(51) Int. Cl.

| | |
|---|---|
| ***A61B 8/08*** | (2006.01) |
| ***A61B 8/12*** | (2006.01) |
| ***A61B 34/10*** | (2016.01) |
| ***A61B 34/20*** | (2016.01) |
| ***A61M 25/01*** | (2006.01) |
| ***G16H 10/60*** | (2018.01) |
| ***G16H 20/40*** | (2018.01) |
| ***G16H 30/40*** | (2018.01) |
| ***G16H 40/67*** | (2018.01) |
| ***G16H 50/50*** | (2018.01) |

(52) U.S. Cl.

CPC ............ *A61B 8/466* (2013.01); *A61B 8/5223* (2013.01); *A61B 34/10* (2016.02); *G16H 10/60* (2018.01); *G16H 20/40* (2018.01); *G16H 30/40* (2018.01); *G16H 40/67* (2018.01); *G16H 50/50* (2018.01); *A61B 8/0841* (2013.01); *A61B 2034/102* (2016.02); *A61B 2034/2065* (2016.02); *A61M 2025/0166* (2013.01)

(56) References Cited

U.S. PATENT DOCUMENTS

| | | | | |
|---|---|---|---|---|
| 9,406,142 | B2 | 8/2016 | Gorman, III et al. | |
| 9,675,450 | B2 | 6/2017 | Schornik et al. | |
| 11,257,397 | B2 | 2/2022 | Markin | |
| 11,432,875 | B2 | 9/2022 | Camus et al. | |
| 11,547,486 | B1 * | 1/2023 | Roh | G16H 50/50 |
| 11,551,355 | B2 | 1/2023 | Jackson et al. | |
| 2008/0146919 | A1 | 6/2008 | Camus et al. | |
| 2012/0022843 | A1 * | 1/2012 | Ionasec | G06T 13/20 703/11 |
| 2017/0084029 | A1 * | 3/2017 | Piazza | G06T 7/62 |
| 2020/0129145 | A1 | 4/2020 | Abbasi | |
| 2020/0397511 | A1 | 12/2020 | Ishrak et al. | |
| 2021/0128163 | A1 | 5/2021 | Osypka | |
| 2022/0273268 | A1 * | 9/2022 | Chapelle | A61B 8/543 |
| 2023/0206603 | A1 * | 6/2023 | Zhang | G06V 10/44 382/100 |
| 2024/0164786 | A1 | 5/2024 | Slaughter et al. | |
| 2024/0261029 | A1 * | 8/2024 | Casey | A61B 34/10 |

FOREIGN PATENT DOCUMENTS

| | | | | |
|---|---|---|---|---|
| DE | 102009016481 | A1 | 10/2010 | |
| WO | WO-2014180972 | A2 * | 11/2014 | A61B 34/10 |
| WO | 2014210299 | A1 | 12/2014 | |

OTHER PUBLICATIONS

K R Steffner et al Deep learning for transesophageal echocardiography view classification Scientific Reports vol. 14, Article No. 11 (2024).

Majd E Hemam et al Left Atrial Appendage Closure with the Watchman Device Using Intracardiac vs Transesophageal Echocardiography: Procedural and Cost Considerations. Heart Rhythm. Author manuscript; available in PMC: Mar. 1, 2020.

Yiting Fan et al "Journal of the American Society of Echocardiographyvol. 32, Issue 6, Jun. 2019, pp. 708-719.e1" Device Sizing Guided by Echocardiography-Based Three-Dimensional Printing Is Associated with Superior Outcome after Percutaneous Left Atrial Appendage Occlusion.

P Burlina et al Patient-Specific Modeling and Analysis of the Mitral Valve Using 3D-TEE "Part of the book series: Lecture Notes in Computer Science ((LNIP,vol. 6135))N. Navab and P. Jannin (Eds.): IPCAI 2010, LNCS 6135, pp. 135-146, 2010".

* cited by examiner

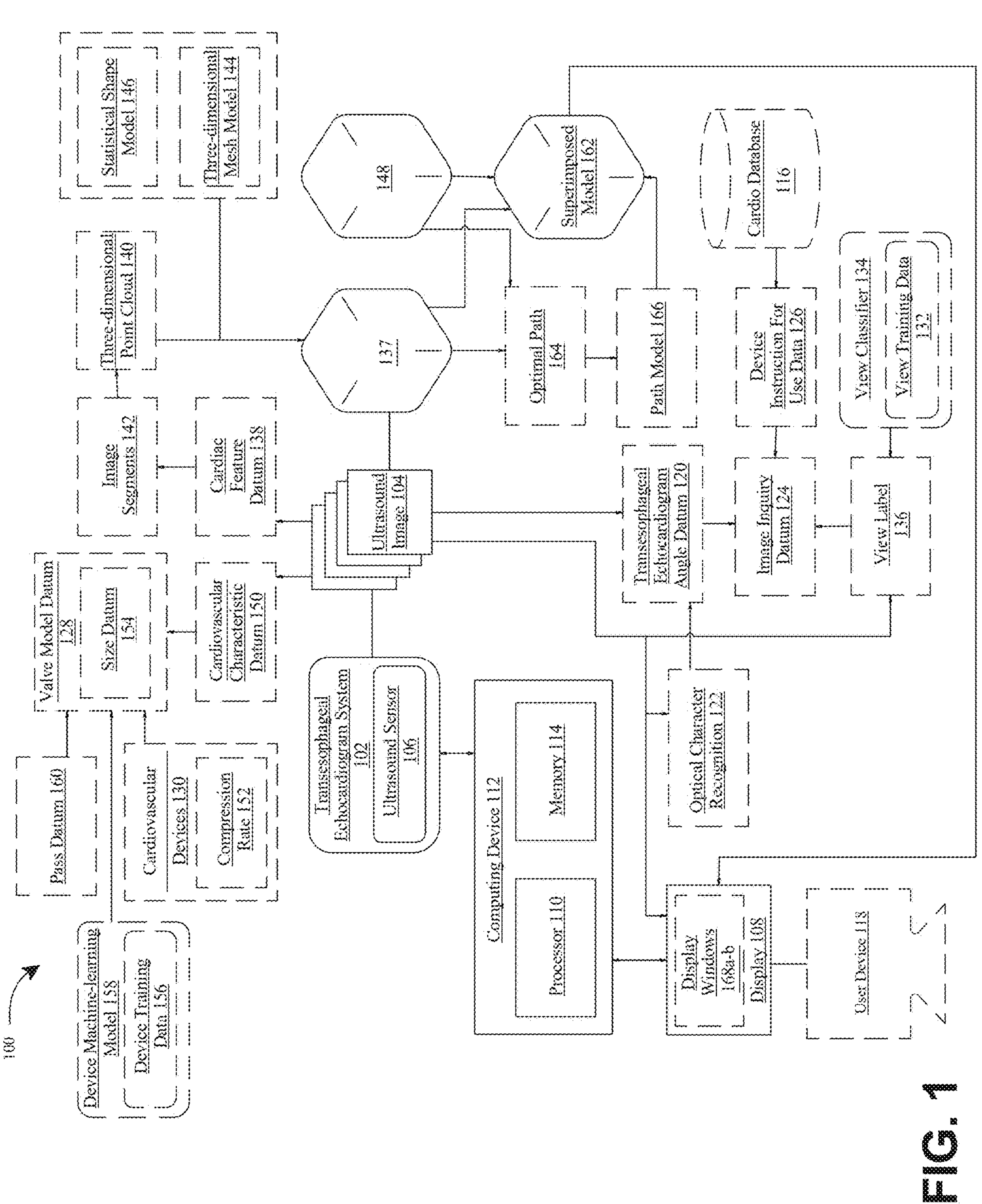

100
Device Machine-learning Model 158
Device Training Data 156
Pass Datum 160
Cardiovascular Devices 130
Compression Rate 152
Valve Model Datum 128
Size Datum 154
Cardiovascular Characteristic Datum 150
Image Segments 142
Cardiac Feature Datum 138
Three-dimensional Point Cloud 140
Statistical Shape Model 146
Three-dimensional Mesh Model 144
Transesophageal Echocardiogram System 102
Ultrasound Sensor 106
Ultrasound Image 104
137
148
Computing Device 112
Processor 110
Memory 114
Optimal Path 164
Superimposed Model 162
Path Model 166
Transesophageal Echocardiogram Angle Datum 120
Optical Character Recognition 122
Display Windows 168a-b
Display 108
User Device 118
Image Inquiry Datum 124
Device Instruction For Use Data 126
Cardio Database 116
View Label 136
View Classifier 134
View Training Data 132
FIG. 1

1300
Storage Device
Medium
Instructions
1324
1328
1320
Display
1336
Display Adaptor
1352
Input Device
1332
1312
1316
Instructions
Processors
1320
1304
Peripheral Interface(s)
1356
Input/ Output System
Instructions
1320
1308
Network Interface
1340
Network
1344
Remote Device
1348

SYSTEM AND METHOD FOR TRANSESOPHAGEAL ECHOCARDIOGRAM-GUIDED IMPLANTATION OF A VALVE DEVICE

CROSS-REFERENCE TO RELATED APPLICATIONS

This application claims the benefit of priority of U.S. Provisional Patent Application Ser. No. 63/705,376, filed on Oct. 9, 2024, and titled "METHODS AND SYSTEMS FOR TRANSESOPHAGEAL ECHOCARDIOGRAM GUIDED IMPLANTATION OF LEFT ATRIAL APPENDAGE CLOSURE DEVICE," which is incorporated by reference herein in its entirety.

FIELD OF THE INVENTION

The present invention generally relates to the field of implantation of valve devices. In particular, the present invention is directed to systems and methods for transesophageal echocardiogram-guided implantation of a valve device.

BACKGROUND

Heart valve replacement is a surgical procedure in which a diseased heart valve is removed and replaced with a new one to improve blood flow and heart function. It is performed when a valve is damaged or dysfunctional due to conditions like stenosis (narrowing of the valve) or regurgitation (leaking of the valve). Current systems lack the proper structure to localize catheters and valves in order to aid in proper placement of the valve during surgical procedures.

SUMMARY OF THE DISCLOSURE

In an aspect, a system for transesophageal echocardiogram-guided implantation of a valve device is described. The system includes at least a transesophageal echocardiogram system including at least an ultrasound sensor configured to be located within an esophagus of a patient and detect at least an ultrasound image as a function of cardiac tissue of the patient. The system further includes a computing device configured to receive the at least an ultrasound image, generate at least a 3D cardiac model representative of a heart of the patient as a function of the at least an ultrasound image wherein the at least an ultrasound image includes a two-dimensional image of the heart of the patient, determine a valve model datum as a function of the 3D cardiac model, receive at least valve model representative of at least a cardiovascular device to be placed within the patient as a function of the valve model datum and display the at least a 3D cardiac model and the at least a valve model.

In another aspect, a method for transesophageal echocardiogram-guided implantation of a valve device is described. The method includes detecting, by at least a transesophageal echocardiogram system, at least an ultrasound image, wherein the at least a transesophageal echocardiogram system includes at least an ultrasound sensor configured to be located within an esophagus of a patient and detect the at least an ultrasound image as a function of cardiac tissue of the patient and receiving, by at least a computing device, the at least an ultrasound image. The method further includes generating, by the at least a computing device, at least a 3D cardiac model representative of a heart of the patient as a function of the at least an ultrasound image wherein the at least an ultrasound image includes a two-dimensional image of the heart of the patient, determining, by the at least a computing device, a valve model datum as a function of the 3D cardiac model, receiving, by the at least a computing device, at least valve model representative of at least a cardiovascular device to be placed within the patient as a function of the valve model datum and displaying, by the at least a computing device, the at least a 3D cardiac model and the at least a valve model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 1 illustrates a block diagram of an exemplary system for transesophageal echocardiogram-guided implantation of a valve device;

Figure 2:
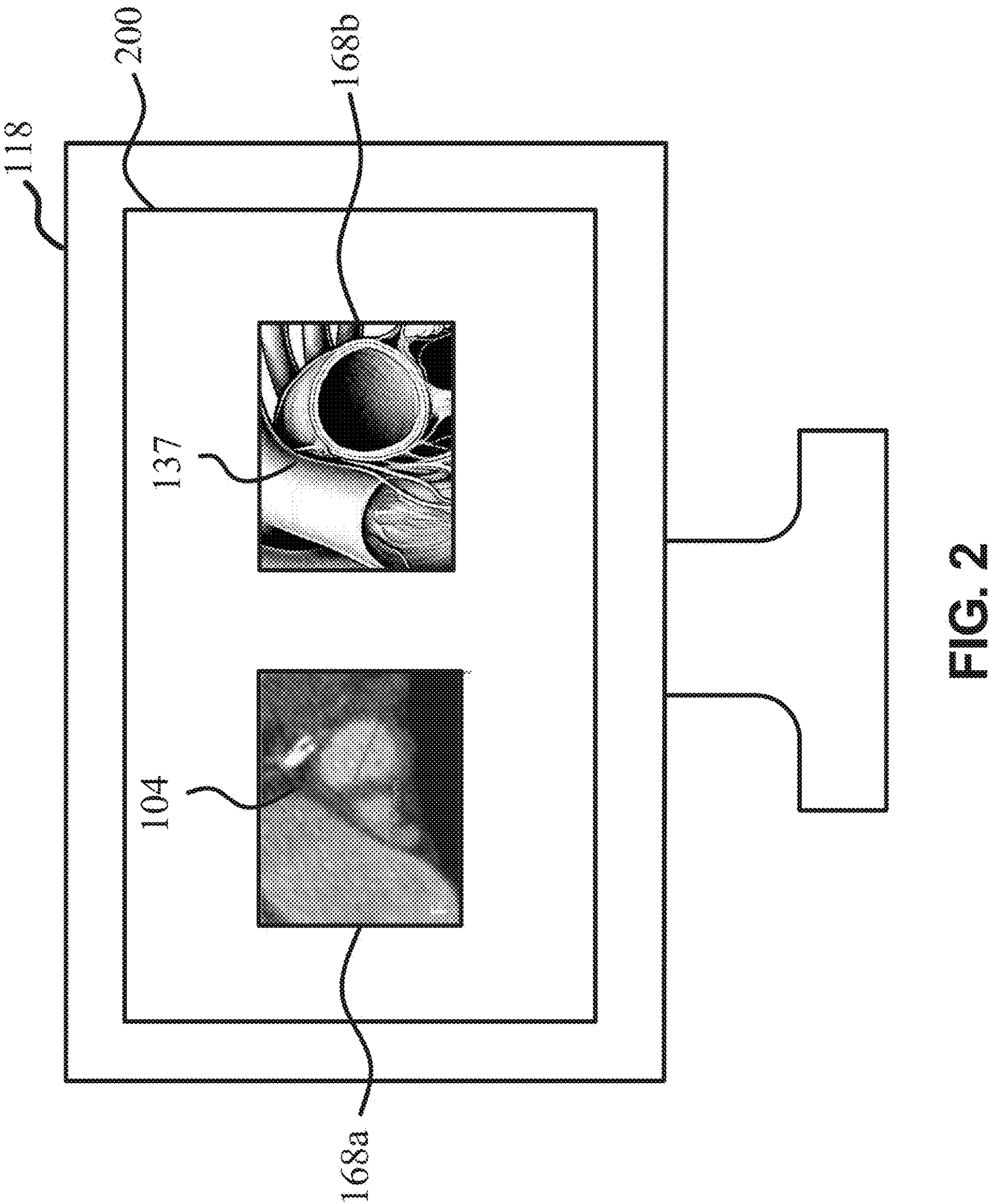
FIG. 2 illustrates an exemplary display used during planning of implantation of a cardiovascular device, according to some embodiments.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for transesophageal echocardiogram-guided implantation. In an embodiment, the present disclosure includes at least a transesophageal echocardiogram system configured to receive at least an ultrasound image and a computing device configured to generate at 3D cardiac model representative of a patient's heart, determine a valve model datum, receive a valve model and display the valve model and the 3D cardiac model Aspects of the present disclosure can be used to aid in implantation of cardiovascular devices and/or monitor already implemented devise such heart valves. Aspects of the present disclosure can also be used to determine which cardiovascular devices may be a correct fit for the patient. This is due in part at least to determination of a valve model datum. Exemplary embodiments illustrating aspects of the present disclosure are described below in the context of several specific examples.

Heart valve repair is a surgical procedure to restore function to a damaged heart valve, often preserving the patient's natural valve tissue. It is usually preferred over valve replacement when possible because it maintains the natural valve structure and function, potentially leading to better long-term outcomes and reduced need for anticoagulation therapy. Heart valve repair may include processes such as Annuloplasty, commissurotomy, leaflet repair, Chordae Tendineae and Papillary Muscle Repair, Decalcification, pericardial path and/or the like.

Referring now to FIG. 1, a block diagram of an exemplary system 100 for transesophageal echocardiogram guided implantation of a valve device is illustrated. System 100 includes at least a transesophageal echocardiogram (TEE) system 102. For the purposes of this disclosure, a "transesophageal echocardiography (TEE) system" is a system designed to perform transesophageal echocardiography. For the purposes of this disclosure, "transesophageal echocardiography" is a medical imaging technique in which an ultrasound transducer is inserted into the esophagus to produce images of the heart and surrounding structures. In one or more embodiments, TEE system 102 may include a combination of specialized hardware and software designed to facilitate transesophageal echocardiography by positioning an ultrasound probe (e.g., ultrasound transducer) within esophagus of a patient, close to a heart of the patient. As the esophagus is proximate to the heart, a TEE system 102 can detect ultrasound image 104 of cardiac tissue of a patient. In one or more embodiments, TEE system 102 may include a TEE probe (endoscope). The TEE probe is a long, flexible device equipped with an ultrasound transducer (ultrasound sensor 106) at its tip. Ultrasound transducer can emit high-frequency sound waves and capture the echoes reflected from cardiac structures to produce detailed images (ultrasound image 104). In a non-limiting example, TEE probe may be inserted into the patient's esophagus, where the TEE probe may be connected to an ultrasound machine, which processes signals from ultrasound transducer to generate images of the heart. In one or more embodiments, TEE system 102 may be communicatively connected to at least a display 108. The display disclosed herein is further described in detail below. Additional disclosure related to TEE system 102 is further described in detail with respect to FIG. 5.

With continued reference to FIG. 1, TEE system 102 includes at least an ultrasound sensor 106 configured to be located within an esophagus of a patient and detect at least an ultrasound image 104 as a function of cardiac tissue of the patient for the purposes of this disclosure, an "ultrasound sensor" is a device that uses ultrasonic waves. In a non-limiting example, ultrasound sensor 106 may measure the distance to an object using ultrasonic sound waves. For the purposes of this disclosure, a "sensor" is a device that produces an output signal for the purpose of sensing a physical phenomenon. For example, and without limitation, sensor may transduce a detected phenomenon, such as without limitation, temperature, voltage, current, pressure, speed, motion, light, moisture, sound waves, and the like, into a sensed signal. Sensor may output the sensed signal. Sensor may include any computing device as described in the entirety of this disclosure and configured to convert and/or translate a plurality of signals detected into electrical signals for further analysis and/or manipulation. Electrical signals may include analog signals, digital signals, periodic or aperiodic signal, step signals, unit impulse signal, unit ramp signal, unit parabolic signal, signum function, exponential signal, rectangular signal, triangular signal, sinusoidal signal, sinc function, or pulse width modulated signal. Any datum captured by sensor may include circuitry, computing devices, electronic components or a combination thereof that translates into at least an electronic signal configured to be transmitted to another electronic component. In a non-limiting embodiment, sensor may include a plurality of sensors included in a sensor suite. In one or more embodiments, and without limitation, sensor may include a plurality of sensors. Sensor may include an ultrasound sensor 106.

With continued reference to FIG. 1, in one or more embodiments, ultrasound sensor 106 may include an electrode. For the purposes of this disclosure, an "electrode" is a conductive material or element that facilitates the transmission and reception of electrical signals associated with ultrasound waves. In a non-limiting example, electrode may detect and record electrical activity; for instance, but not limited to, the heart's electrical signals. For example, and without limitation, electrode may generate ultrasonic sound waves, from which ultrasound sensor 106 receives the ultrasonic waves and transmit ultrasound image 104 related to the ultrasonic waves to processor 110. In one or more embodiments, ultrasound sensor 106 may include a transducer. For the purposes of this disclosure, a "transducer" is a component of an ultrasound sensor that converts one form of energy into another. In a non-limiting example, transducer may operate on a principle of piezoelectricity, where piezoelectric material can convert electrical energy into mechanical vibration (i.e. ultrasonic waves) and vice versa. In one or more embodiments, ultrasound sensor 106 may include a transceiver. For the purposes of this disclosure, a "transceiver" is a combined unit of a transmitter and a receiver. In a non-limiting example, transceiver may transmit ultrasonic waves and receive echoes.

With continued reference to FIG. 1, for the purposes of this disclosure, "ultrasound image" is a visual representation generated by reflection of high-frequency sound waves off internal body structures. In a non-limiting example, ultrasound image 104 may include visual representation of a heart examined through esophagus. As a non-limiting example, ultrasound image 104 may include distance between sensor and surrounding tissue or organs. In one or more embodiments, ultrasound sensor 106 may detect ultrasound image 104 in a plurality of angles. In a non-limiting example, ultrasound image 104 may include a plurality of distances between sensor and a heart in different angles. For example, and without limitation, when ultrasound sensor 106 moves around within an esophagus, ultrasound sensor 106 receives a plurality of distances between ultrasound sensor 106 and organ and generate ultrasound image 104 using the plurality of distances.

With continued reference to FIG. 1, in one or more embodiments, ultrasound sensor may be configured to capture an ultrasound image 104 of a cardiac tissue of a patient. "Cardiac tissue" as described in this disclosure refers to any portion of an individual's heart. For example and without limitation, cardiac tissue may include heart valves, chambers, protective sacs and/or the like. In a non-limiting example, ultrasound image 104 may include an image of a heart before implantation of a cardiovascular device, during implantation of a cardiovascular device and/or after implantation of a cardiovascular device. For example, and without limitation, ultrasound image 104 may include an image of a valve of a heart that may not be working properly. In one or more embodiments, ultrasound sensor may be configured to capture the internal surroundings of a patient's heart.

With continued reference to FIG. 1, system 100 includes a computing device 112. Computing device 112 includes a processor 110 communicatively connected to a memory 114. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device 112. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, in one or more embodiments, computing device 112 may include any computing device as described in this disclosure, including without limitation a microcontroller, microprocessor, digital signal processor (DSP) and/or system on a chip (SoC) as described in this disclosure. Computing device 112 may include, be included in, and/or communicate with a mobile device such as a mobile telephone or smartphone. Computing device 112 may include a single computing device operating independently, or may include two or more computing devices operating in concert, in parallel, sequentially or the like; two or more computing devices may be included together in a single computing device or in two or more computing devices. Computing device 112 may interface or communicate with one or more additional devices as described below in further detail via a network interface device. Network interface device may be utilized for connecting computing device 112 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 112. Computing device 112 may include but is not limited to, for example, a computing device or cluster of computing devices in a first location and a second computing device or cluster of computing devices in a second location. Computing device 112 may include one or more computing devices dedicated to data storage, security, distribution of traffic for load balancing, and the like. Computing device 112 may distribute one or more computing tasks as described below across a plurality of computing devices of computing device, which may operate in parallel, in series, redundantly, or in any other manner used for distribution of tasks or memory between computing devices. Computing device 112 may be implemented, as a non-limiting example, using a "shared nothing" architecture.

With continued reference to FIG. 1, in one or more embodiments, computing device 112 may be designed and/or configured to perform any method, method step, or sequence of method steps in any embodiment described in this disclosure, in any order and with any degree of repetition. For instance, computing device 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 112 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, memory 114 contains instructions configuring processor 110 to receive at least an ultrasound image 104. In one or more embodiments, processor 110 may receive ultrasound image 104 from TEE system 102. In one or more embodiments, processor 110 may receive ultrasound image 104 from a cardio database 116. In one or more embodiments, system 100 may include a Cardio database 116. As used in this disclosure "cardio database" is a data structure configured to store data associated with one or more patient's hearts. In one or more embodiments, Cardio database 116 may include inputted or calculated information and datum related to a patient'; s heart such as chambers, blood vessels and/or the like. In one or more embodiments, a datum history may be stored in Cardio database 116. As a non-limiting example, the datum history may include real-time and/or previous inputted data related to the patient's heart. As a non-limiting example, Cardio database 116 may include instructions from a user, who may be an expert user, a past user in embodiments disclosed herein, or the like, where the instructions may include examples of the data related to a patient's heart.

With continued reference to FIG. 1, in one or more embodiments, processor 110 may be communicatively connected with Cardio database 116. For example, and without limitation, in one or more embodiments, Cardio database 116 may be local to processor 110. In another example, and without limitation, Cardio database 116 may be remote to processor 110 and communicative with processor 110 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 110 connect directly, dynamically, and non-hierarchically to as many other computing devices as possible. A "network topology" as used in this disclosure is an arrangement of elements of a communication network. The network may use an immutable sequential listing to securely store Cardio database 116. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in one or more embodiments, Cardio database 116 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in one or more embodiments, processor 110 may receive ultrasound image 104 from a user device 118. For the purposes of this disclosure, a "user device" is any device a user use to input data. For the purposes of this disclosure, a "user" is an individual or entity that uses an apparatus. As a non-limiting example, a user may include a surgeon, doctor, medical professional, and the like. As a non-limiting example, user device 118 may include a laptop, desktop, tablet, mobile phone, smart phone, smart watch, kiosk, screen, smart headset, or things of the like. In one or more embodiments, user device 118 may include an interface configured to receive inputs from user. In one or more embodiments, user may manually input any data into computing device 112 using user device 118. In one or more embodiments, user may have a capability to process, store or transmit any information independently.

With continued reference to FIG. 1, in one or more embodiments, receiving at least an ultrasound image 104 may include extracting at least a TEE angle datum 120 from at least an ultrasound image 104 using an optical character recognition. For the purposes of this disclosure, a "transesophageal echocardiogram angle datum" is a data element indicating a value that represents the angular orientation of an ultrasound sensor. In one or more embodiments, TEE angle datum 120 may be angular orientation of an ultrasound sensor 106 relative to a reference axis or plane (e.g., the anatomical position of a heart). As a non-limiting example, TEE angle datum 120 may include TEE probe's imaging angle, such as 0°, 45°, 90°, or 135°, which may determine the plane of the ultrasound slice captured during imaging.

With continued reference to FIG. 1, ultrasound image 104 may be received through a TEE procedure. In one or more embodiments, ultrasound image may be received from TEE system 102 and/or ultrasound sensor 106 during a TEE procedure. TEE procedure is described in further detail below in reference to at least FIG. 2. In one or more embodiments, ultrasound image may include TEE echocardiogram data as described in reference to at least FIG. 2.

With continued reference to FIG. 1, in one or more embodiments, processor 110 may analyze ultrasound image 104 to find TEE angle datum 120 using optical character recognition (OCR) 122. In one or more embodiments, ultrasound image 104 may include a plurality of words related to position and orientation of ultrasound sensor 106 within esophagus. For the purposes of this disclosure, "optical character recognition" is a technology that enables the recognition and conversion of printed or written text into machine-encoded text. In one or more embodiments, the at least a processor 110 may be configured to recognize a keyword using the OCR 122 to find the TEE angle datum 120. As used in this disclosure, a "keyword" is an element of word or syntax used to identify and/or match elements to each other. In one or more embodiments, the at least a processor 110 may transcribe much or even substantially all ultrasound images 104.

With continued reference to FIG. 1, in one or more embodiments, optical character recognition 122 or optical character reader (OCR) may include automatic conversion of images of written (e.g., typed, handwritten or printed text) into machine-encoded text. In one or more embodiments, recognition of a keyword from ultrasound image 104 may include one or more processes, including without limitation optical character recognition (OCR) 122, optical word recognition, intelligent character recognition, intelligent word recognition, and the like. In one or more embodiments, OCR 122 may recognize written text, one glyph or character at a time. In one or more embodiments, optical word recognition may recognize written text, one word at a time, for example, for languages that use a space as a word divider. In one or more embodiments, intelligent character recognition (ICR) may recognize written text one glyph or character at a time, for instance by employing machine-learning processes. In one or more embodiments, intelligent word recognition (IWR) may recognize written text, one word at a time, for instance by employing machine-learning processes.

With continued reference to FIG. 1, in one or more embodiments, OCR 122 may be an "offline" process, which analyses a static document or image frame. In one or more embodiments, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information may make handwriting recognition more accurate. In one or more embodiments, this technology may be referred to as "online" character recognition, dynamic character recognition, real-time character recognition, and intelligent character recognition.

With continued reference to FIG. 1, in one or more embodiments, OCR processes may employ pre-processing of ultrasound image 104. Pre-processing process may include without limitation de-skew, de-speckle, binarization, line removal, layout analysis or "zoning," line and word detection, script recognition, character isolation or "segmentation," and normalization. In one or more embodiments, a de-skew process may include applying a transform (e.g., homography or affine transform) to the ultrasound image 104 to align text. In one or more embodiments, a de-speckle process may include removing positive and negative spots and/or smoothing edges. In one or more embodiments, a binarization process may include converting an image from color or greyscale to black-and-white (i.e., a binary image). Binarization may be performed as a simple way of separating text (or any other desired image component) from a background of image component. In one or more embodiments, binarization may be required for example if an employed OCR algorithm only works on binary images. In one or more embodiments, a line removal process may include removal of non-glyph or non-character imagery (e.g., boxes and lines). In one or more embodiments, a layout analysis or "zoning" process may identify columns, paragraphs, captions, and the like as distinct blocks. In one or more embodiments, a line and word detection process may establish a baseline for word and character shapes and separate words, if necessary. In one or more embodiments, a script recognition process may, for example in multilingual documents, identify script allowing an appropriate OCR algorithm to be selected. In one or more embodiments, a character isolation or "segmentation" process may separate signal characters, for example character-based OCR algorithms. In one or more embodiments, a normalization process may normalize aspect ratio and/or scale of image component.

With continued reference to FIG. 1, in one or more embodiments an OCR process may include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

With continued reference to FIG. 1, in one or more embodiments, an OCR process may include a feature extraction process. In one or more embodiments, feature extraction may decompose a glyph into a feature. Exemplary non-limiting features may include corners, edges, lines, closed loops, line direction, line intersections, and the like. In one or more embodiments, feature extraction may reduce dimensionality of representation and may make the recognition process computationally more efficient. In one or more embodiments, extracted feature may be compared with an abstract vector-like representation of a character, which might reduce to one or more glyph prototypes. General techniques of feature detection in computer vision are applicable to this type of OCR 122. In one or more embodiments, machine-learning processes like nearest neighbor classifiers (e.g., k-nearest neighbors algorithm) may be used to compare image features with stored glyph features and choose a nearest match. OCR 122 may employ any machine-learning process described in this disclosure, for example machine-learning processes described with reference to FIG. 6. Exemplary non-limiting OCR software may include Cuneiform and Tesseract. Cuneiform may include a multi-language, open-source optical character recognition system originally developed by Cognitive Technologies of Moscow, Russia. Tesseract may include free OCR software originally developed by Hewlett-Packard of Palo Alto, California, United States.

With continued reference to FIG. 1, in one or more embodiments, OCR 122 may employ a two-pass approach to character recognition. A first pass may try to recognize a character. Each character that is satisfactory may be passed to an adaptive classifier as training data. The adaptive classifier then may get a chance to recognize characters more accurately as it further analyzes ultrasound image 104. Since the adaptive classifier may have learned something useful a little too late to recognize characters on the first pass, a second pass may be run over the ultrasound image 104. Second pass may include adaptive recognition and use characters recognized with high confidence on the first pass to recognize better remaining characters on the second pass. In one or more embodiments, two-pass approach may be advantageous for unusual fonts or low-quality image components where visual verbal content may be distorted. Another exemplary OCR software tool may include OCRopus. OCRopus development is led by German Research Centre for Artificial Intelligence in Kaiserslautern, Germany. In one or more embodiments, OCR software may employ neural networks.

With continued reference to FIG. 1, in one or more embodiments, OCR 122 may include post-processing. For example, OCR accuracy may be increased, in one or more embodiments, if output is constrained by a lexicon. A lexicon may include a list or set of words that are allowed to occur in a document. In one or more embodiments, a lexicon may include, for instance, all the words in the English language, or a more technical lexicon for a specific field. In one or more embodiments, an output stream may be a plain text stream or file of characters. In one or more embodiments, an OCR process may preserve an original layout of visual verbal content. In one or more embodiments, near-neighbor analysis can make use of co-occurrence frequencies to correct errors, by noting that certain words are often seen together. For example, "Washington, D.C." is generally far more common in English than "Washington DOC." In one or more embodiments, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, in one or more embodiments, processor 110 may generate an image inquiry datum 124 as a function of the at least a TEE angle datum 120 and device instruction for use (IFU) data 126 retrieved from Cardio database 116. For the purposes of this disclosure, an "image inquiry datum" is a data element that inquires additional ultrasound images. In one or more embodiments, image inquiry datum 124 may include a control signal that is transmitted to TEE system 102 to obtain necessary additional ultrasound images 104. In a non-limiting example, if processor 110 determines that ultrasound images in specific views or specific angles and/or a number of ultrasound images are missing based on device IFU data 126, processor 110 may request additional ultrasound images 104 from TEE system 102. In one or more embodiments, image inquiry datum 124 may include a notification for a user. In a non-limiting example, if processor 110 determines that ultrasound images in specific views or specific angles and/or a number of ultrasound images are missing based on device IFU data 126, processor 110 may generate a notification and may transmit to a user to operate TEE system 102 to generate additional ultrasound images 104 more and/or in the specific views or specific angles. In a non-limiting example, image inquiry datum 124 may be configured to query additional ultrasound images 104 to a user of at least a TEE system 102 through at least a display 108.

With continued reference to FIG. 1, for the purposes of this disclosure, "device Instructions for Use (IFU) data" is data related to procedural guidelines or specifications associated with cardiovascular device. As a non-limiting example, device IFU data 126 may include usage instructions, imaging requirements, and the like. For example, and without limitation, device IFU data 126 may include specific views or angles of ultrasound images 104 necessary for a placement of cardiovascular device on a coronary artery. A "cardiovascular device" as described in this disclosure refers to a medical device that is used in the management of diseases or conditions affecting the heart. For example, and without limitation, cardiovascular device may include heart valves. In one or more embodiments, cardiovascular device may be used for heart valve repair as described in this disclosure. In one or more embodiments, cardiovascular device may be used to stabilize and reshape the ring around heart valves to restore normal valve function. In one or more embodiments, cardiovascular device may be use to reinforce the areas of a heart valve that may be weakened or damaged. In one or more embodiments, cardiovascular device may be implanted within the heart of a patient in order to improve the functioning of one or more arteries and/or valves. In one or more embodiments, cardiovascular device may include a stent. A "Stent" as described in this disclosure is a tube configured to be implanted within the heart of a patient and used to keep the arteries of veins open. In one or more embodiments, stent may include a bare-metal stent, a drug-eluding stent, a biodegradable stent, a covered stent, a graft stent, a self-expanding stent, a ballon-expandable sent and/or the like. In one or more embodiments, cardiovascular device may include a heart valve. A "heart valve" as described int this disclosure is prosthetic calve that is configured to replace or repair a damaged heart valve. In one or more embodiments, heart valve may include heart valves, such as but not limited to, tilting disc valves, stented tissue valves, stent less tissue valves, homograft, autografts, transcatheter heart valves, aortic valves, mitral valves, tricuspid valves, pulmonary valves and/or the like. In one or more embodiments, IFU data 126 may include specific view of angles needed for a medical professional to properly implant cardiovascular device within a patient. In one or more embodiments, device IFU data 126 may be stored in a Cardio database 116. In one or more embodiments, processor 110 may retrieve device IFU data 126 from Cardio database 116 as a function of valve model datum 128. As a non-limiting example, processor may retrieve device IFU data 126 that is related to a cardiovascular device selected specifically for a patient. In one or more embodiments, cardiovascular device may be used to keep arteries or veins open. In one or more embodiments, cardiovascular device may include prosthetic valves that replace or repair damaged valves.

With continued reference to FIG. 1, in one or more embodiments, receiving at least an ultrasound image 104 may include generating view training data 132, wherein the view training data 132 may include exemplary ultrasound images correlated to exemplary view labels, training a view classifier 134 using the view training data 132, classifying the at least an ultrasound image 104 to at least a view label 136 using the trained view classifier 134 and generating an image inquiry datum 124 as a function of the view label 136 and device IFU data 126. For the purposes of this disclosure, a "view label" is an identifier associated with an imaging perspective or orientation of a heart captured during a transesophageal echocardiography. As a non-limiting example, view label 136 may include mid-esophageal four-chamber view, mid-esophageal bicaval view, mid-esophageal long-axis view, mid-esophageal left atrial appendage view, transgastric short-axis view, transgastric two-chamber view, aortic valve short-axis view, and the like. In one or more embodiments, view label 136 may be retrieved from Cardio database 116. In one or more embodiments, user may manually input view label 136 of ultrasound images 104.

With continued reference to FIG. 1, in one or more embodiments, view training data 132 may be stored in Cardio database 116. For the purposes of this disclosure, "view training data" is data containing correlations that a machine-learning process may use to model relationships between ultrasound images and view labels. In one or more embodiments, view training data 132 may be received from one or more users, Cardio database 116, external computing devices, and/or previous iterations of processing. As a non-limiting example, view training data 132 may include instructions from a user, who may be an expert user, a past user in embodiments disclosed herein, or the like, which may be stored in memory and/or stored in Cardio database 116, where the instructions may include labeling of training examples. In one or more embodiments, view training data 132 may be updated iteratively on a feedback loop. As a non-limiting example, processor 110 may update view training data 132 iteratively through a feedback loop as a function of ultrasound image 104, TEE angle datum 120, view label 136, device IFU data 126, or the like. In one or more embodiments, processor 110 may be configured to generate a view classifier 134. For the purposes of this disclosure, a "view classifier" is a machine-learning model as defined below, such as a data structure representing and/or using a mathematical model, neural net, or program generated by a machine learning algorithm known as a "classification algorithm," as described in further detail below, that sorts ultrasound images into view labels. In a non-limiting example, generating view classifier 134 may include training, retraining, or fine-tuning view classifier 134 using view training data 132 or updated view training data 132. In one or more embodiments, processor 110 may be configured to determine view label 136 using view classifier 134 (i.e. trained or updated view classifier 134). In one or more embodiments, generating training data and training machine-learning models may be simultaneous.

With continued reference to FIG. 1, memory 114 contains instructions configuring processor 110 to generate at least a 3D cardiac model 137 representative of a patient's heart as a function of at least an ultrasound image 104. For the purposes of this disclosure, a "three-dimensional cardiac model" is a three-dimensional representation of a patient's heart and/or surrounding structures. In some embodiments, 3D cardiac model may include peripheral vasculature. "Peripheral vasculature," for the purposes of this disclosure, is a structure or structures of blood vessels surrounding or in the immediate vicinity of the heart. In a non-limiting example, 3D cardiac model 137 may include a 3D voxel occupancy representation (VOR). As used in this disclosure, a "3D voxel occupancy representation (VOR)" of an anatomical object is a 3D digital representation of a spatial structure of the anatomical object, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such density/occupancy as described below. In an embodiment, each voxel of plurality of voxels within 3D VOR may represent a specific portion of heart. In one or more embodiments, voxel may be a smallest distinguishable box-shaped part (i.e., 1px·1 px·1 px) of a three-dimensional image. In one or more embodiments, each voxel of plurality of voxels within VOR may be represented as a cube or rectangular prism (although other shapes may be used in specialized applications). Each voxel may include a size that determines a resolution of the 3D image or model. In an embodiment, smaller voxels may provide higher resolution; however, it may require more computational resources (e.g., RAM) for processor 110 to process.

In an embodiment, and still referring to FIG. 1, each voxel of plurality of voxels within VOR may include one or more embedded values. As used herein, "embedded values" refers to specific numerical or categorical data associated with each voxel. In one or more embodiments, embedded values may represent various attributes or characteristics of the corresponding portion of heart that voxel represents. In a non-limiting example, embedded values may include density values, intensity values, texture information, or any other quantitative measures that provide insights into the underlying cardiac tissue. Such embedded values may be derived from set of ultrasonic images or other imaging modalities used to generate 3D cardiac model 137. In one or more embodiments, embedded values may be utilized, by processor 110, to differentiate between different types of cardiac tissues, such as myocardial tissue, blood vessels, or chambers. Embedded values may also facilitate the visualization of dynamic cardiac functions, for example, and without limitation, blood flow or heart beating by encoding temporal information such as timestamps within plurality of voxels.

In one or more embodiments, and still reference to FIG. 1, one or more embedded values, such as, without limitations, occupancy, or density, may be derived from ultrasound images 104 described herein by processor 110. In a non-limiting example, determining occupancy status of each voxel of plurality of voxels may include converting set of ultrasonic images 104 to a set of binary images and determining occupancy status of each voxel as a function of the structure of interest's binary value. In one or more embodiments, occupancy status may include a value representing the likelihood of occupancy of the corresponding heart tissue. In another non-limiting example, density may be calculated, by processor 110, for each voxel as a function of the echogenicity of one or more pixels on a given ultrasound image 104, wherein, the brightness of the given ultrasonic image may be analyzed since different tissues reflect ultrasound waves differently.

With continued reference to FIG. 1, generating 3D cardiac model 137 of heart may include generating a 3D array. In one or more embodiments, processor 110 may divide 3D space into a grid of plurality of voxels, each with specific x, y, and z coordinates as embedded values. Each element of 3D array may correspond to a voxel. In one or more embodiments, 3D array may allow for easy access and manipulation of plurality of voxels, enabling various analyses, visualizations, and transformations either described or not described herein. In a non-limiting example, embedded values may include a density of the tissue at a specific location of a patient's body derived from one or more ultrasonic images of ultrasound images 104.

Additionally, or alternatively, and still referring to FIG. 1, 3D cardiac model 137 of heart may include a 3D grid embedded values described herein of plurality of voxels (e.g., tissue density, blood flow velocity, echogenicity or acoustic properties, and any other biophysical properties). As used in this disclosure, a "3D grid" refers to a 3D data structure that divides a given volume (e.g., volume of a heart) into a plurality of discrete units called cells (i.e., volume elements). In an embodiment, each cell within 3D grid may be associated with a distinct voxel.

In yet another embodiment, and still referring to FIG. 1, cells may be continuous, meaning that one or more cells may represent one or more continuous regions of space rather than discreate, separate units. In a non-limiting example, instead of being uniform, mapped presence indicator and/or other embedded values may vary continuously across different cells or cell's volume. In such embodiment, processor 110 may use interpolation to estimate other (unknown) embedded values within a range based on existing values such as known embedded values at specific points, thereby allowing for smooth transitions between cells. Exemplary interpolation methods may include, without limitation, linear interpolation, cubic interpolation, and/or the like. For example, and without limitation, if the corners of a cell have known values interpolation can be used to estimate the values at any point within the cell based on those corner values.

In a non-limiting example, and still referring to FIG. 1, 3D cardiac model 137 of heart may include a 3D grid having a plurality of cells e.g., voxels, wherein each cell may contain a continuous range of values representing tissue density, blood flow velocity, or other properties (i.e., embedded values). Processor 110 may be configured to apply trilinear or tricubic interpolation to estimate tissue density within each cell based on presence indicator or other known values at the cell's boundaries, since tissue densities change gradually; Such 3D grid may provide a smooth, continuous representation of heat's internal structures, allowing for more nuanced analysis and visualization as described below. In a further embodiment, 3D grid with continuous cells may be additionally used in fluid dynamics simulations.

With continued reference to FIG. 1, in some case, embedded values may be mapped to 3D grid as a function of array masking, wherein specific array or grid may be selected to modify based on one or more pre-defined criteria. In a non-limiting example, processor 110 may generate a mask e.g., a binary array that defines which voxels or cells are affected. Mask may be used to select or modify specific voxels or cells based on certain attributes; for instance, and without limitation, processor 110 may use mask to isolate the left atrium (LA) within the heart focusing the analysis on that specific region. Such mask may include a criteria defined by specific density thresholds that distinguish the LA's tissue (i.e., voxels representing LA in 3D grid) from surrounding structures (i.e., neighboring voxels). In one or more embodiments, such mask may further include a binary mask, wherein each voxel in the 3D gird may be assigned a first presence indicator such as 1 if the voxel meets the criteria for the LA and a second presence indicator such as 0 if it does not. In one or more embodiments, mask may be directly applied to 3D grid, selecting, or modifying voxels or cells, thereby enabling processor 110 to highlight, exclude, or otherwise manipulate specific parts of heart within 3D grid. Processor 110 may then perform an element-wise multiplication between 3D grid and the mask. Continuing from the previous non-limiting example, voxels corresponding to the LA (wherein the mask value is 1) may retain their original values, while other voxels (where the mask value is 0) may be set to 0 or other specific value (i.e., excluded or masked out).

With continued reference to FIG. 1, ultrasound image 104 may include a two-dimensional representation of a patient's heart. In one or more embodiments, two-dimensional representation may include two-dimensional images. In one or more embodiments, two-dimensional images may include a flat, planar representation containing rows and columns of pixel values, such as a photograph or a digital drawing. In one or more embodiments, ultrasound image may be created by converting ultrasound waves into a two-dimensional image. In one or more embodiments, brightness and shading within ultrasound image 104 may be determined based on the intensity of returning echoes. In one or more embodiments, intensity of returning echoes may depend on the density and type of tissue. In one or more embodiments, TEE system 102 may be configured to receive ultrasound waves from ultrasound sensor and generate ultrasound images 104 as result. In one or more embodiments, 3D cardiac model includes a three-dimensional interpolation of the two-dimensional image of ultrasound image 104. A "three-dimensional interpolation," as described in this disclosure refers to a process of using data from a two dimensional image or from textual data to generate or estimate values in a three dimensional space. For example, and without limitation, images may be used to construct a three-dimensional model of the image. In one or more embodiments, a three dimensional model may include a length width and height, whereas a two dimensional image and/or model may include a length and height. In one or more embodiments, processor 110 may use any process as described in this disclosure to generate 3D cardiac model, wherein 3D cardiac model includes a three dimensional interpolation of a two dimensional image.

With continued reference to FIG. 1, in one or more embodiments, 3D grid may include one or more cardiac feature datums 138 extracted from ultrasound image 104 of heart. As used in this disclosure, "cardiac feature datums" are specific characteristics or attributes related to a heart. In one or more embodiments, cardiac feature datum 138 may include spatial arrangement, shape, size, or texture of a heart. In one or more embodiments, cardiac feature datums 138 may include one or more embedded values described herein and their combinations thereof. In a non-limiting example, cardiac feature datum 138 may be represented numerically as a vector, a metric or other mathematical constructs that capture specific spatial characteristics. In one or more embodiments, cardiac feature datums 138 may also be visualized as contours, surfaces, or other geometric representations. In an embodiment, cardiac feature datums 138 may be extracted using edge detection, texture analysis, or other image processing techniques (e.g., cleaning and enhancing images, image segmentation, and/or the like). In another embodiment, one or more machine learning models, such as convolutional neural networks (CNNs) as described in further detail below, may be used to extract complex cardiac feature datums 138. The cardiac feature datum 138 is further described below. In one or more embodiments, cardiac feature datum 138 may further include the size and/or placement of arteries, identification of various cardiovascular devices and/or the like. In one or more embodiments, cardiac feature datum 138 may indicate a particular portion of the heart, such as for example, a specific valve, a specific chamber, a specific cardiovascular device and/or the like.

Still referring to FIG. 1, as used in this disclosure, a "vector" is a data structure that represents one or more a quantitative values and/or measures of one or more cardiac feature datums 138. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes.

Still referring to FIG. 1, in a non-limiting example, one or more cardiac feature datums 138 may include one or more shape features (i.e., characteristics related to the shape of specific cardiac structures), such as curvature, surface area, volume, and/or the like. In another non-limiting example, one or more cardiac feature datums 138 may include one or more texture features (i.e., characteristics related to the texture or pattern within cardiac tissues, as seen ultrasound image 104), such as gray-level co-occurrence matrix (GLCM) features representing the texture of heart muscle tissue. In another non-limiting example, one or more cardiac feature datums 138 may include one or more orientation features (i.e., characteristics related to the orientation or alignment of cardiac structures), such as the angle or alignment of the septum within the heart. In a further non-limiting example, one or more cardiac feature datums 138 may include one or more edge and boundary features (i.e., Characteristics related to the edges or boundaries between different cardiac structures or tissues), such as edge detection features highlighting the boundary between the myocardium and the cardiac chambers. As an ordinary person skilled in the art, upon reviewing the entirety of this disclosure, will be aware of various cardiac feature datums extracted from ultrasound image 104 in consistent with this disclosure.

With continued reference to FIG. 1, in one or more embodiments, system 100 may include a computer vision model configured to generate 3D cardiac model 137 of heart. A "computer vision model," for the purpose of this disclosure, is a computation model designed to interpret and make determinations based on visual data. In an embodiment, computer vision model may process ultrasound images 104, to make a determination about a scene, space, and/or object in heart. In a non-limiting example, computer vision model may be used for registration of plurality of voxels within a 3D space. In one or more embodiments, registration may include image processing described herein, such as without limitation object recognition, feature detection, edge/corner detection, and the like. Non-limiting example of feature detection may include scale invariant feature transform (SIFT), Canny edge detection, Shi Tomasi corner detection, and the like. In one or more embodiments, registration may include one or more transformations to orient an ultrasonic image relative a 3D coordinate system; exemplary transformations include without limitation, homography transforms and affine transforms. In an embodiment, registration of ultrasonic image to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto the ultrasonic image; however, a third dimension of registration, representing depth and/or a z axis, may be detected by utilizing depth-sensing techniques such as Doppler imaging. Alternatively, the third dimension may be inferred from the known geometry and orientation of the imaging device (e.g., ultrasound sensor 106 of TEE system 102), or through the application of one or more machine learning models trained to interpret depth from the two-dimensional projection.

With continued reference to FIG. 1, processor 110 may use a machine learning module to implement one or more algorithms or generate one or more machine learning models, such as a cardiac modeling model to generate 3D cardiac model 137 of heart. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from a database, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In a further embodiment, training data may include previous outputs such that one or more machine learning models iteratively produces outputs.

Still referring to FIG. 1, machine learning module may be used to generate anatomy modeling model and/or any other machine learning models, such as, shape identification model as described in further detail below, using training data. Cardiac modeling model may be trained by correlated inputs and outputs of training data. Training data may be data sets that have already been converted from raw data whether manually, by machine, or any other method. In an embodiment, generating 3D cardiac model 137 of heart may include receiving anatomy training data, wherein the anatomy training data may include a plurality of ultrasound images as input and a plurality of 3D cardiac models as output. In one or more embodiments, anatomy training data may be received from Cardio database 116 or other databases. In other cases, anatomy training data may be collected by a data acquisition unit from external sources such as one or more medical equipment's e.g., imaging devices or diagnostic tools, wherein the data acquisition may be configured as an intermediary between the data source and machine learning module. In one or more embodiments, anatomy training data may include a plurality of ultrasound images correlated to a plurality of 3D cardiac models. In one or more embodiments, a particular ultrasound images 104 within anatomy training data may be correlated to a particular 3D cardiac model. In one or more embodiments, anatomy training data may further include a plurality of ultrasound images 104 correlated to a plurality of cardiac models. In an embodiment, a particular ultrasound images 104 may be correlated to a particular cardiac model. In one or more embodiments anatomy training data may include TEE diagrams, Cardiac CTs, ECG signals and/or ultrasonic images as an input and correlated 3D representations of heart With continued reference to FIG. 1, in an embodiment, anatomy modeling model may include a deep neural network (DNN). As used in this disclosure, a "deep neural network" is defined as a neural network with two or more hidden layers. Neural network is described in further detail below with reference to FIGS. 6-8. In a non-limiting example, anatomy modeling model may include a convolutional neural network (CNN). Generating 3D cardiac model 137 of heart may include training CNN using anatomy training data and generating 3D cardiac model 137 as a function of ultrasound images 104 using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In one or more embodiments, CNN may include, without limitation, a deep neural network (DNN) extension. Mathematical (or convolution) operations performed in the convolutional layer may include convolution of two or more functions, where the kernel may be applied to input data e.g., ultrasound images 104 through a sliding window approach. In one or more embodiments, convolution operations may enable processor 110 to detect local/global patterns, edges, textures, and any other cardiac feature datums 138 described herein within each ultrasound images 104. Cardiac feature datums 138 may be passed through one or more activation functions, such as without limitation, Rectified Linear Unit (ReLU), to introduce non-linearities into the processing step of generating 3D cardiac model 137 of heart. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the spatial dimensions of cardiac feature datum maps by applying downsampling, such as max-pooling or average pooling, to small, non-overlapping regions of one or more cardiac feature datums 138.

Still referring to FIG. 1, CNN may further include one or more fully connected layers configured to combine cardiac feature datums 138 extracted by the convolutional and pooling layers. In one or more embodiments, one or more fully connected layers may allow for higher-level pattern recognition. In a non-limiting example, one or more fully connected layers may connect every neuron (i.e., node) in its input to every neuron in its output, functioning as a traditional feedforward neural network layer. In one or more embodiments, one or more fully connected layers may be used at the end of CNN to perform high-level reasoning and produce the final output such as, without limitation, a 3D cardiac model 137 of heart. Further, each fully connected layer may be followed by one or more dropout layers configured to prevent overfitting, and one or more normalization layers to stabilize the learning process described herein.

With continued reference to FIG. 1, CNN may further include a 3D CNN, wherein the 3D CNN, unlike standard 2D CNN, may include utilization of one or more 3D convolutions which allow them to directly process 3D data, thereby enabling processor 110 to generate 3D structures such as 3D cardiac model 137 of heart using the 3D CNN. In a non-limiting example, 3D CNN may include one or more 3D filters (i.e., kernels) that move through the ultrasound images 104 in three dimensions and capturing spatial relationships in x, y, and z axis. Similar to 3D convolutions, 3D CNN may further include one or more 3D pooling layers that may be used to reduce the dimensionality of ultrasonic images while preserving cardiac feature datums 138 as described above. Additionally, or alternatively, an encoder-decoder structure may be implemented (extended to 3D), by processor 110, in 3D CNN, wherein the encoder-decoder structure includes an encoding path that captures the context and a decoding path that enables precise localization in a same manner as U-net as described above. Such encoder-decoder structures may also include a plurality of skip connections, allowing 3D CNN to use information from multiple resolutions to improve the process of generating 3D cardiac model 137 of heart.

With continued reference to FIG. 1, in an embodiment, training the cardiac modeling model (i.e., CNN) may include selecting a suitable loss function to guide the training process. In a non-limiting example, a loss function that measures the difference between the predicted 3D VORs and the ground truth 3D structure e.g., CT-based anatomical object models may be used, such as, without limitation, mean squared error (MSE) or a custom loss function may be designed for one or more embodiments described herein. Additionally, or alternatively, optimization algorithms, such as stochastic gradient descent (SGD), may then be used to adjust the anatomy modeling model's parameters to minimize such loss. In a further non-limiting embodiment, instead of directly predicting 3D cardiac model 137, cardiac modeling model may be trained as a regression model to predict embedded values described herein for each voxel of plurality of voxels within a 3D grid. Additionally, CNN may be extended with additional deep learning techniques, such as recurrent neural networks (RNNs) or attention mechanism, to capture additional features and/or data relationships within input data. These extensions may further enhance the accuracy and robustness of the anatomical object modeling.

With continued reference to FIG. 1, in one or more embodiments, generating at least a 3D cardiac model 137 may include extracting at least a cardiac feature datum 138 from at least an ultrasound image 104 and segmenting the at least an ultrasound image 104 into a plurality of image segments 142. As a non-limiting example, extracting cardiac feature datum 138 may include structural elements like left atrium, left atrial appendage, mitral valve, aortic valve, ventricular walls, and the like. In one or more embodiments, extracting a cardiac feature datum 138 may include isolating and identifying cardiac feature datum 138 from ultrasound image 104 using image processing or machine learning techniques. For the purposes of this disclosure, an "image segment" is a section of an ultrasound image. In one or more embodiments, image segment 142 may include a section of an ultrasound image that has been partitioned based on shared visual or anatomical properties (e.g., cardiac feature datum 138). In a non-limiting example, in a 2D image, segmenting ultrasound image 104 may include all the pixels that make up cardiac feature datum 138, while in a 3D context, it would encompass all the voxels (3D pixels) that constitute cardiac feature datum 138. In one or more embodiments, processor 110 may segment 3D cardiac model 137 and segmenting 3D cardiac model 137 may include extracting cardiac feature datum 138 from 3D cardiac model 137 and segmenting 3D cardiac model 137 as a function of cardiac feature datum 138.

With continued reference to FIG. 1, processor 110 may be configured to segment ultrasound image 104 in order to isolate cardiac features and record them as cardiac feature datum 138. In one or more embodiments, only portions of a patient's heart relative to implementation of a cardiovascular device may be contained whereas other portions may be removed. In one or more embodiments, With continued reference to FIG. 1, in one or more embodiments, processor 110 may be configured to analyze ultrasound image and/or 3D cardiac model 137 using machine vision system to determine cardiac feature datum 138. For the purposes of this disclosure, a "machine vision system" is a type of technology that enables a computing device to inspect, evaluate and identify still or moving images. For example, in one or more embodiments a machine vision system may be used for world modeling or registration of objects within a space. In one or more embodiments, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In one or more embodiments, a machine vision process may operate image classification and segmentation models, such as without limitation by way of machine vision resource (e.g., OpenMV or TensorFlow Lite). A machine vision process may detect motion, for example by way of frame differencing algorithms. A machine vision process may detect markers, for example blob detection, object detection (e.g., cardiac feature datum 138), face detection, and the like.

With continued reference to FIG. 1, in one or more embodiments, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and $\phi$ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level.

With continued reference to FIG. 1, in one or more embodiments, segmenting an ultrasound image 104 and/or 3D cardiac model 137 may include training a segmentation model with segmentation training data, wherein the segmentation training data may include exemplary ultrasound image and/or 3D cardiac model correlated to exemplary segmented ultrasound image and/or 3D cardiac model and segmenting a ultrasound image 104 and/or 3D cardiac model 137 using the trained segmentation model. For the purposes of this disclosure, a "segmentation model" is a machine learning or deep learning model designed to partition an image into multiple segments or regions, each corresponding to different objects or parts of an object within the image. In one or more embodiments, segmentation model may assign a label to each pixel in an image (e.g., ultrasound image 104 and/or 3D cardiac model 137) such that pixels with the same label share certain characteristics, such as belonging to the same cardiac feature datum 138 or region. As a non-limiting example, segmentation model may include a neural network. For the purposes of this disclosure, "segmentation training data" is data containing correlations that a machine-learning process may use to model relationships between echo depth maps and segmented echo depth maps. In a non-limiting example, a segmentation model may analyze ultrasound image 104 and/or 3D cardiac model 137 to identify and delineate the boundaries of cardiac feature datum 138. This may include finding the set of coordinates $\{(X_i, Y_i)\}$ that represent the pixels or voxels making up the cardiac feature datum 138. In one or more embodiments, processor 110 may segment ultrasound image and/or 3D cardiac model 137 based on cardiac feature datum 138. In one or more embodiments, segmentation training data may be stored in Cardio database 116. In one or more embodiments, segmentation training data may be received from one or more users, Cardio database 116, external computing devices, and/or previous iterations of processing. As a non-limiting example, segmentation training data may include instructions from a user, who may be an expert user, a past user in embodiments disclosed herein, or the like, which may be stored in memory and/or stored in Cardio database 116, where the instructions may include labeling of training examples. In one or more embodiments, segmentation training data may be updated iteratively on a feedback loop. As a non-limiting example, processor 110 may update segmentation training data iteratively through a feedback loop as a function of output of feature extraction model, ultrasound image 104, 3D cardiac model 137, and the like. In one or more embodiments, processor 110 may be configured to generate segmentation model. In a non-limiting example, generating segmentation model may include training, retraining, or fine-tuning segmentation model using segmentation training data or updated segmentation training data. In one or more embodiments, processor 110 may be configured to segment ultrasound image 104 and/or 3D cardiac model 137 using segmentation model (i.e. trained or updated segmentation model).

With continued reference to FIG. 1, in one or more embodiments, generating at least a 3D cardiac model 137 may include generating a 3D point cloud 140 as a function of a plurality of image segments 142 and generating a 3D mesh model 144 of at least a 3D cardiac model 137 as a function of the 3D point cloud 140. For the purposes of this disclosure, a "three dimensional point cloud" is a collection of data points in space, each represented by its x, y, and z coordinates. In one or more embodiments, 3D point cloud 140 may capture the geometry of cardiac feature datums 138, providing a comprehensive 3D representation. In one or more embodiments, the construction of 3D point cloud 140 may integrate cardiac feature datums 138 and/or image segments 142 from multiple frames. In a non-limiting example, when cardiac feature datums 138 and/or image segments 142 (z) is added to pixel coordinates to convert them into 3D points (x, y, z), all the 3D points can be aggregated to form 3D point cloud 140. In one or more embodiments, 3D cardiac model 137 may include 3D mesh model 144. For the purposes of this disclosure, a "three-dimensional mesh model" is a mathematical and geometric representation of the surface of a three-dimensional object. In one or more embodiments, 3D mesh model 144 may be constructed using a network of vertices, edges, and faces. In one or more embodiments, vertices may define points in 3D space, the edges may connect pairs of vertices, and the faces, in the form of triangles or quadrilaterals, may create a polygonal surface that represents the shape of the object (heart). In one or more embodiments, processor 110 may generate a mesh representing cardiac shape as a function of 3D voxel occupancy representation. Processor 110 may be configured to display, using display, a mesh to a user. Additional disclosure related to generation of 3D cardiac model 137 may be found in U.S. Nonprovisional application Ser. No. 18/787,196, filed on Jul. 29, 2024, and entitled "APPARATUS AND METHOD FOR OBJECT POSE ESTIMATION IN A MEDICAL IMAGE," and U.S. Nonprovisional application Ser. No. 18/938,980, filed on Nov. 6, 2024, and entitled "APPARATUS AND METHOD OF DETERMINING A CARDIAC IMPLANT SIZE," the entirety of which is incorporated herein by reference.

With continued reference to FIG. 1, in one or more embodiments, 3D cardiac model 137 may include a statistical shape model 146. As used in this disclosure, a "statistical shape model (SSM)" is a data structure representing, including, and/or utilizing a mathematical model that captures principal modes of variation in shape across a population of cardiac anatomies. SSM 146 captures a plurality of heart models associated with a plurality of patients. In one or more embodiments, SSM 146 may be used to capture the variability in anatomical structures among different patients; for instance, SSM 146 of the human heart may be constructed from a plurality of heart images of a plurality of individuals. In one or more embodiments, 3D cardiac model 137 generated by SSM model may capture the "average" heart shape and main ways in which heart shapes may vary among the plurality of individuals. In one or more embodiments, 3D cardiac model 137 generated by SSM model may capture the "average" of the plurality of anatomical objects in which anatomical objects may vary among plurality of individuals. In one or more embodiments, SSM 146 may be generated by processor 110 as a function of a set of labeled example shapes, each in a form of point-based representations (3D point clouds 140) or meshes. In one or more embodiments, example shapes may be represented in a 3D voxel occupancy representation (VOR).

With continued reference to FIG. 1, generating 3D cardiac model 137 may include generating 3D cardiac model 137 using a point completion model. For the purposes of this disclosure, a "point completion model" is an algorithm that is configured to fill in missing data within a point cloud. In some embodiments, point completion model may include one or more deep learning models. In some embodiments, point completion model may include point-based methods. Point based methods may include modeling each point individually using multilayer perceptron (MLP) layers. In some embodiments, features may be learned from raw input point cloud data. This may reduce reliance on prior information and/or manually set parameters. In some embodiments, point-based methods may use an encoder-decoder architecture. In some embodiments, encoder-decoder may include an end-to-end cascaded neutral network. In some embodiments, point completion model may use a selective focus approach. A selective focus approach may include an attention mechanism. Attention is an adaptive mechanism that is used to capture information and assign higher weights to important data. In some embodiments, point completion model may include an unsupervised 3D point cloud capsule network that uses autoencoders to process sparse point clouds and preserve the spatial arrangement. In some embodiments, attention mechanisms may be used to enhance the resolution and fill in missing parts. In some embodiments, point completion model may use a view-guided approach. Relying on a single view may be susceptible to scene and temporal limitations, which can result in lost details. In some embodiments, a view-guided framework (ViPC) that retrieves absent global shape information from alternative single-view images may be used. By including additional single-view images, ViPC may provide global structural prior information for point cloud completion. In some embodiments, point completion model may use a point completion network (PCN)-assisted approach. Some deep-learning methods usually discretize 3D data into voxels that act directly on the convolution operations. Instead, in some embodiments, a multi-stage point cloud completion network (MSPCN) with crucial set oversight, incorporating a cascading upsampling module to achieve high-resolution outcomes gradually may be used. The vital sets for each stage may be used for oversight, thereby generating more informative and valuable intermediary outputs for the subsequent stage. In some embodiments, a skeleton-bridged PCN (SK-PCN) to complement shapes by locally scanning them may be used. Initially the SK-PCN may forecast their 3D skeleton to attain a universal structure, and completing surfaces by learning the shifts in the skeleton points. In some embodiments a point enhancement network (ME-PCN) may use the "void" in the 3D shape space to approximate rough but complete and coherent surface points and then produce fine-grained surface details in the refinement stage. A local-to-local strategy may be used in some embodiments, and an attentional point cloud aggregation module may be used to aggregate local scans to complete point clouds.

With continued reference to FIG. 1, additionally, 3D reconstruction of ultrasound images 104 into 3D cardiac models 137 is described in a number of co-owned patent applications listed below. Each of these applications are incorporated herein by reference in their entirety: U.S. Nonprovisional application Ser. No. 18/818,034, filed on Aug. 28, 2024, and entitled "APPARATUS AND METHODS FOR GENERATING A THREE-DIMENSIONAL (3D) MODEL OF AN ANATOMICAL OBJECT VIA MACHINE-LEARNING," which is a continuation-in-part of Non-provisional application Ser. No. 18/750,411 filed on Jun. 21, 2024, and entitled "APPARATUS AND METHODS FOR GENERATING A THREE-DIMENSIONAL (3D) MODEL OF AN ANATOMICAL OBJECT VIA MACHINE-LEARNING," which is a continuation of Non-provisional application Ser. No. 18/376,688 filed on Oct. 4, 2023, and entitled "APPARATUS AND METHODS FOR GENERATING A THREE-DIMENSIONAL (3D) MODEL OF CARDIAC ANATOMY VIA MACHINE-LEARNING," the entirety of which are incorporated herein by reference and U.S. Nonprovisional application Ser. No. 18/817,870, filed on Aug. 28, 2024, and entitled "APPARATUS AND METHODS FOR SYNTHESIZING MEDICAL IMAGES," which is a continuation-in-part of Non-provisional application Ser. No. 18/509,520, filed on Nov. 15, 2023, and entitled "APPARATUS AND METHODS FOR SYNTHESIZING MEDICAL IMAGES," the entirety of which are incorporated herein by reference and U.S. Non-provisional application Ser. No. 18/818,152, filed on Aug. 28, 2024, and entitled "APPARATUS AND METHOD FOR GENERATING A THREE-DIMENSIONAL (3D) MODEL OF CARDIAC ANATOMY BASED ON MODEL UNCERTAINTY," which is a continuation-in-part of Non-provisional application Ser. No. 18/426,604, filed on Jan. 30, 2024, and entitled "APPARATUS AND METHOD FOR GENERATING A THREE-DIMENSIONAL (3D) MODEL OF CARDIAC ANATOMY BASED ON MODEL UNCERTAINTY," the entirety of which are incorporated herein by reference and U.S. Non-provisional application Ser. No. 18/818,311 filed on Aug. 28, 2024, and entitled "APPARATUS AND METHOD FOR GENERATING A THREE-DIMENSIONAL (3D) MODEL OF CARDIAC ANATOMY WITH AN OVERLAY," which is a continuation-in-part of Non-provisional application Ser. No. 18/395,087 filed on Dec. 22, 2023, and entitled "APPARATUS AND METHOD FOR GENERATING A THREE-DIMENSIONAL (3D) MODEL OF CARDIAC ANATOMY WITH AN OVERLAY," the entirety of which are incorporated herein by reference and U.S. Non-provisional application Ser. No. 18/648,176 filed on Apr. 26, 2024, and entitled "APPARATUS AND METHODS FOR VISUALIZATION WITHIN A THREE-DIMENSIONAL MODEL USING NEURAL NETWORKS," the entirety of which is incorporated herein by reference.

With continued reference to FIG. 1, in one or more embodiments, generating 3D cardiac model representative of patient's heart may include receiving a generic 3D model. A "Generic 3D model for the purposes of this disclosure is a three-dimensional representation of a heart not associated to any particular individual. For example, and without limitation, generic 3D model may include a digitally created three dimensional model of a heart. In one or more embodiments, generic 3D model may include density, measurements and/or the like of determined averages of individuals' hearts. In one or more embodiments, generic 3D model may include an aggregation of a plurality of ultrasound images that are used to create a 3D model representative of the aggregate. In one or more embodiments, generic 3D model may be received from any database as described in this disclosure. In one or more embodiments, generic 3D model may include a 3D cardiac model representing values of an average organ based on a plurality of ultrasound images. In one or more embodiments, generic 3D model may include a digital representation of an organ having no issues. For example, and without limitation, generic 3D model may include a digital representation of a heart having no blockages within the arteries. In one or more embodiments, generic 3D model may include a digital representation of an organ that is deemed to be a healthy organ. In one or more embodiments, generic 3D model may be used a reference for other digital models representing a heart. In one or more embodiments, generic 3D model may include one or more values of an organ that is deemed to be healthy. In one or more embodiments, the values may include tissue density, valve diameter, heart shape and/or any other values that are described in reference to 3D cardiac model. In one or more embodiments, values may be categorized based on cardiac features, wherein each cardiac feature within generic 3D model may contain its own values. In one or more embodiments, generic 3D model may contain generic cardiac feature datum, wherein generic cardiac feature datum includes cardiac feature datum of generic 3D model.

With continued reference to FIG. 1, processor 110 may be configured to generate 3D cardiac model as a function of generic model. In one or more embodiments, processor may be configured to receive generic 3D model and refine generic 3D model to create 3D cardiac model.

With continued reference to FIG. 1, processor 110 may be configured to generate a refined organ model as a function of refinement. As used in this disclosure, a "refined organ model" refers to an organ model customized to reflect a patient's organ. For example, and without limitation, refined organ model may include 3D cardiac model. In one or more embodiments, generic 3D model may be refined to create 3D cardiac model and/or refined model. In an embodiment, refined organ model may be derived from generic 3D model and adjusted based on sensor data and/or ultrasound images 104. In such embodiment, refined organ model may include a deformed organ model as described above. In a non-limiting example, 3D VOR may indicate a need of adjustment to generic 3D model to match a subject's unique geometry. SSM may then be configured to generate refined organ model that accurately captures such specific organ anatomy based on generic 3D model and 3D VOR. In other cases, generic 3D model may not need any refinement; for instance, and without limitation, if generic 3D model already align perfectly with subject's organ, no deformation or adjustment would be necessary, thereby resulting in refined organ model and/or 3D cardiac model that is identical to generic 3D model.

Still referring to FIG. 1, in some cases, the refinement process may also include the incorporation of more detailed features and textures based on sensor data such as ultrasound images 104 thereof, enhancing the realism and specificity of generic 3D model. In an embodiment, SSM may be integrated with one or more additional models such as, without limitation, texture models, appearance models, or functional models to generate refined organ model and/or 3D cardiac model. In some cases, such integration may result in refined organ model that reflects not just the geometry but also the biomechanical properties or blood flow dynamics within organ. In a non-limiting example, texture of the myocardium may be modeled, by integrating texture models with SSM, to represent the fibrous nature of the heart muscle. In another non-limiting example, appearance of blood vessels, including color variations and translucency, may be modeled, by integrating appearance models with SSM.

With continued reference to FIG. 1, alternatively, refining generic 3D model may include adjusting generic 3D model based on set of shape parameters. In an embodiment, processor 110 may be configured to map set of shape parameters to SSM. The mapping process may define how generic 3D model should be adjusted to represent specific subject's organ anatomy. In a non-limiting example, shape parameters may include one or more numeric values indicating a particular thick ventricular wall, processor 110 may configure SSM to adjust generic 3D model to reflect such characteristic. In an embodiment, generating refined organ model may involve generating a 3D mesh or grid that accurately represents the shape defined by set of shape parameters; for instance, and without limitation, processor 110 may be configured to generate a 3D mesh for left ventricle with vertices and edges positioned according to specific curvature and thickness defined by set of shape parameters using SSM.

With continued reference to FIG. 1, processor 110 may be configured to input generic 3D model into one or more machine learning models, such as for example, cardiac modeling model, as described in this disclosure to create 3D cardiac model 137. In one or more embodiments, processor 110 may utilize a machine vision system to modify generic 3D model in order to create 3D cardiac model. In one or more embodiments, processor 110 may be configured to identify one or more anomalies within ultrasound image. An "anomaly" for the purposes of this disclosure refers to a datapoint of set of data points that deviates from an expected pattern or result. For example, and without limitation, anomaly within ultrasound image 104 may include the presence of a lump that may not ordinarily be present within a healthy heart. In another non-limiting example, anomaly may include a particular size of the heart, or various portions thereof that may not conform to sizes typically associated with a healthy heart. In one or more embodiments, anomaly may include any change in density, size, thickness and/or the like of various feature datum within ultrasound image in comparison to generic 3D model. In one or more embodiments, anomalies may be used to compare ultrasound image 104 to generic 3D model and determine differences in distances, densities and/or the like between a patient's heart and that of a Generic model. In one or more embodiments, generic 3D model may include generic cardiac feature Datum, wherein generic cardiac feature datum includes cardiac feature datum of generic 3D model. In one or more embodiments, processor 110 may identify anomalies within ultrasound image by comparing cardiac feature datum to generic cardiac feature datum. In an embodiment, differences in values between a particular cardiac feature datum and generic cardiac feature datum may indicate the presence of one or more anomalies. In one or more embodiments, processor 110 may be configured to modify generic 3D model based on the identified anomalies in order to generate 3D cardiac model. In one or more embodiments, generic 3D model may be modified in any way as described in this disclosure. In one or more embodiments, generic 3D model may be modified in any way similar to the generation of 3D cardiac model as described in this disclosure. In one or more embodiments, processor may be configured to generate 3D cardiac model by adjusting values within generic 3d model, such as for example, a thickness, a density, contours, surfaces and/or other geometric representations. In one or more embodiments, creating cardiac 3D model may include modifying one or more voxels and/or 3D grid embedded values within generic 3D model. In one or more embodiments, generic 3D model may include a plurality fo cardiac features wherein only cardiac features identified as anomalies may be modified. In an embodiment, features not identified within ultrasound images 104 may be given generic cardiac feature datums. In an embodiment, modification of generic 3D model may ensure that values not identified and/or cardiac feature datums not identified may instead be replaced with generic features from within generic 3D model.

With continued reference to FIG. 1, an anomaly may include a spatial distortion. A "Spatial distortion" for the purposes of this disclosure refers to a change in measurement between the patient's heart and a generic heart with generic 3D model. For example, and without limitation, spatial distortion may include a change in length or radius of a ventricle calculated from a comparison between cardiac feature datum and generic cardiac feature datum. In one or more embodiments, spatial distortion may indicate that a sizing of the patient's heart and/or portions thereof may be different from that of Generic 3D model. In one or more embodiment, spatial distortion may be used to generate cardiac 3D model, wherein A 3D grid for example may be modified. In one or more embodiments, spatial distortions may indicate changes in measurement between ultrasound image and generic 3D model, wherein generic 3D model may require modification in order to match the anatomy of the patient. In one or more embodiments, anomaly may include a spatial distortion of at least one cardiac feature of the patient. This may include for example, a difference in measurement of a ventricle, a difference in measurement of a heart chamber and/or the like. In one or more embodiments, 3d cardiac model may be generated by identifying anomalies within ultrasound image 104 and modifying generic 3D model to include and/or account for the anomalies.

With continued reference to FIG. 1, memory 114 contains instructions configuring processor 110 to receive at least a valve model 148 representative of at least a cardiovascular device 130. For the purposes of this disclosure, a "valve model" is a three-dimensional visual representation of a cardiovascular device. In some embodiments, valve model 148 may be consistent with 3D cardiac model 137. In some embodiments, processor 110 may retrieve valve model 148 from a Cardio database 116. In some embodiments, user may manually input valve model 148 into computing device 112. In some embodiments, processor 110 may receive ultrasound image 104 from TEE system 102, wherein the ultrasound image 104 may include an image of a catheter with cardiovascular device entering a right atrium or left atrium or cardiovascular device being placed within a coronary artery, and processor 110 may extract an image of cardiovascular device and generate valve model 148.

With continued reference to FIG. 1, in some embodiments, receiving at least a valve model 148 may include extracting at least a cardiovascular characteristic datum 150 from at least an ultrasound image 104, determining a valve model datum 128 as a function of the at least a cardiovascular characteristic datum 150 and a compression rate 152 of a plurality of cardiovascular devices 130, and generating the at least a valve model 148 as a function of the valve model datum 128. For the purposes of this disclosure, an "cardiovascular characteristic datum" is a data element indicating a value representing one or more properties of the cardiovascular system of an individual. As a non-limiting example, cardiovascular characteristic datum 150 may include diameter, shape, depth, orientation, or geometry of an aortic valve, mitral valve and/or the like. In some embodiments, cardiovascular characteristic datum 150 may be stored in a database. In some embodiments, cardiovascular characteristic datum 150 may be retrieved from database. In some embodiments, user may manually input cardiovascular characteristic datum 150. In some embodiments, processor 110 may determine cardiovascular characteristic datum 150 using machine vision system, image processing techniques, and the like. For the purposes of this disclosure, a "valve model datum" is a data element that indicates a value or set of values describing properties of a cardiovascular device. In some embodiments, valve model datum 128 may include a size datum 154. For the purposes of this disclosure, a "size datum" is a data element that indicates a size of a cardiovascular device. As a non-limiting example, valve model datum 128 may include parameters such as a particular cardiovascular device's nominal size (expanded diameter), its shape or configuration, anchoring features, material used and the like. In a non-limiting example, determining valve model datum 128 may include determining which cardiovascular device of a plurality of cardiovascular devices 130 will best match the anatomy of a patient's heart (cardiovascular characteristic datum 150). For the purposes of this disclosure, a "compression rate" is a percentage difference between the nominal diameter of a cardiovascular device and its deployed diameter once it is placed within a valve or artery. In some embodiments, processor 110 may retrieve compression rate 152 from Cardio database 116. In some embodiments, device IFU data 126 may include compression rate 152 of cardiovascular devices 130. In a non-limiting example, compression rate 152 can be used to ensure that cardiovascular device 130 remains securely anchored while avoiding excessive force that could damage surrounding tissue of cardiovascular system. For example, and without limitation, processor 110 may determine valve model datum 128 as a function of cardiovascular characteristic datum 150 and compression rate 152, where cardiovascular device 130 have a compression rate 152 within a specific range (e.g., 8-20%). In some embodiments, processor 110 may generate valve model 148 that reflects cardiovascular device 130 that is determined by processor 110.

With continued reference to FIG. 1, valve model datum may indicate the sizing, shape and/or orientation of cardiovascular device and/or valve model 148. In an embodiment, processor may determine the sizing needed of the valve model. In one or more embodiments, the sizing of the valve model may be directly correlated to the sizing of cardiovascular device. In one or more embodiments, valve model datum may be used to visually determine the correct size of valve model 148. In one or more embodiments, valve model datum may be determined based on cardiovascular characteristic datum 150. In one or more embodiments, cardiovascular characteristic datum 150 may indicate the radius of an artery, the length of the diseased segment within an arty or valve and/or the like. In an embodiment, valve model datum may include the length of a valve needed to cover a lesion within an artery. In one or more embodiments, valve model datum may indicate the diameter of the valve needed in order to ensure a proper fit within the artery. In one or more embodiments, Aortic valve prostheses may range from 19-29 mm in diameter based on the diameter of the valve associated with the patient. In one or more embodiments, cardiac feature datum and/or cardiovascular characteristic datum 150 indicating pressure gradients and/or flow rates may be used to determine which cardiovascular device to use. In one or more embodiments, valve model datum may indicate the type of cardiovascular device and/or valve model to be used. This may include for example, mechanical valves, transcatheter valves, bare-metal stents, drug-eluding stents and/or the like. In one or more embodiments, the particular type of cardiovascular device chosen may be determined based on the risk of restenosis, wherein for example, a high risk of stenoses may require a metal stent and a lower risk of stenoses may require a drug-eluding stent. In one or more embodiments, the particular type of cardiovascular device may be determined based on a particular medical diagnoses and/or medical condition. For example, and without limitation, an aortic valve may be required to prevent backflow of blood from the aorta into the left ventricle. In another non limiting example, a pulmonary valve may be required to prevent backflow of blood from the pulmonary artery into the right ventricle. In one or more embodiments, valve model datum may be determined as a function of 3D cardiac model.

With continued reference to FIG. 1, in some embodiments, processor 110 may be configured to generate device training data 156. In a non-limiting example, device training data 156 may include correlations between exemplary cardiovascular characteristic data and exemplary valve model datums. In some embodiments, device training data 156 may be stored in Cardio database 116. In some embodiments, device training data 156 may be received from one or more users, Cardio database 116, external computing devices, and/or previous iterations of processing. As a non-limiting example, device training data 156 may include instructions from a user, who may be an expert user, a past user in embodiments disclosed herein, or the like, which may be stored in memory and/or stored in Cardio database 116, where the instructions may include labeling of training examples. In some embodiments, device training data 156 may be updated iteratively on a feedback loop. As a non-limiting example, processor 110 may update device training data 156 iteratively through a feedback loop as a function of cardiovascular characteristic datum 150, valve model datum 128, ultrasound image 104, or the like. In some embodiments, processor 110 may be configured to generate a device machine-learning model 158. In a non-limiting example, generating device machine-learning model 158 may include training, retraining, or fine-tuning device machine-learning model 158 using device training data 156 or updated device training data 156. In some embodiments, processor 110 may be configured to determine valve model datum 128 using device machine-learning model 158 (i.e. trained or updated device machine-learning model 158). In some embodiments, patient, patient's heart or ultrasound image 104 may be classified to a patient cohort using a cohort classifier. Cohort classifier may be consistent with any classifier discussed in this disclosure. Cohort classifier may be trained on cohort training data, wherein the cohort training data may include patient, patient's heart or ultrasound image 104 correlated to patient cohorts. In some embodiments, patient, patient's heart or ultrasound image 104 may be classified to a patient cohort and processor 110 may determine valve model datum 128 based on the patient cohort using a machine-learning module as described in detail with respect to FIG. 6 and the resulting output may be used to update device training data 156. In some embodiments, generating training data and training machine-learning models may be simultaneous.

With continued reference to FIG. 1, in some embodiments, determining valve model datum 128 may include simulating a placement of a plurality of cardiovascular devices 130 within at least a 3D cardiac model 137 as a function of at least a cardiovascular characteristic datum 150 and compression rate 152 and determining the valve model datum 128 as a function of the simulation. In a non-limiting example, processor 110 may use finite element analysis (FEA) or similar computational methods to simulate how cardiovascular devices 130 interacts with the valves or arteries of a patient's heart. In some embodiments, determining valve model datum 128 may include determining a pass datum 160 as a function of at least a cardiovascular characteristic datum 150 and compression rate 152. In some embodiments, generate pass datum 160 for simulation of a placement of a plurality of cardiovascular devices 130 within at least a 3D cardiac model 137. For the purposes of this disclosure, a "pass datum" is a data element that indicates a value representing whether a specific cardiovascular device is deemed suitable for placement within an artery, valve and/or any other section of the cardiovascular system. As a non-limiting example, pass datum 160 may include a position datum that represents spatial orientation and location of cardiovascular device 130 implanted within an artery during a simulation or placement process. As another non-limiting example, pass datum 160 may include an anchor datum that describes the ability of cardiovascular device 130 to anchor securely within an artery. As another non-limiting example, pass datum 160 may include a placement size datum that indicates the dimensions of cardiovascular device 130, such as its expanded diameter, length, or coverage area, ensuring compatibility with the cardiovascular system such as for example, arteries and/or valves and achieving desired compression rate.

With continued reference to FIG. 1, receiving valve model 148 includes receiving valve model as a function of valve model datum. In one or more embodiments, valve model datum may indicate the particular valve model 148 to be used. In one or more embodiments, valve model datum may include a range of sizes that can be used, wherein at least one valve model may be selected that conforms to the range of values. In an embodiment, a database, such as cardio database 116 may include a plurality of valve models, wherein processor 110 may be configured to receive and/or select a valve model that conforms to the values within valve model datum. For example, and without limitation, processor may be configured to select a particular valve in instances in which valve model datum indicates an aortic valve. In another non limiting example, processor may select a particular diameter of a valve based on a diameter listed within valve model datum. In an embodiment, valve model may be representative of at least a cardiovascular device to be placed within the patient. In an embodiment, valve model datum may indicate the particular type of cardiovascular device and/or valve model to be placed within the patient. In one or more embodiments, valve model datum may indicate the correct sizing and/or the correct category of cardiovascular devices (e.g. stents, valves, pacemakers, etc.) to be used. In one or more embodiments, processor 110 may be configured to receive valve model as a function of valve model datum.

With continued reference to FIG. 1, a database such as cardio database 116 may include a plurality of valve models representative of cardiovascular devices. In one or more embodiments, processor may use valve model datum to query database in order to identify at least one available valve model form the plurality of valve models. An "available valve model" as described herein refers to a 3d representation of a cardiovascular device that can be physically acquires and uses for use in implantation. For example and without limitation, available valve model may include a particular aortic valve that the medical professional has within their inventory and can be placed within the patient. In another non limiting example, available valve model may include a 3d representation of a cardiovascular device that is capable of fitting properly within the patient. In one or more embodiments, a database, such as cardio database 116 may include a plurality of valve models, wherein one or more available valve models may be selected for implantation. In one or more embodiments, cardio database may include valve models that correspond to a cardiovascular device that physically exists and can be retrieved by an individual for implantation. In one or more embodiments, database may be populated with available inventory of a hospital, wherein available valve model may include a valve model currently within inventory. In one or more embodiments, database may include a plurality of valve models corresponding to differing sizes, differing types, differing classes and/or the like. In one or more embodiments, processor 110 may be configured to query database in order to identify a valve model suitable for the patient based on the valve model datum. A "query" for the purposes of the disclosure is a string of characters that poses a question or request. In one or more embodiments, query may include a search query. A "search query" for the purposes of this disclosure is a structured request for data. In one or more embodiments, search query may be used to search a database for a particular set of information such as valve models. In one or more embodiments, search query may include conditions for the type of data desired, such as a valve model with a particular diameter and/or length. In one or more embodiments, search query may be in the form of a structured query language (SQL). In one or more embodiments, search query may include the data fields to retrieve, such as for example, diameter, material, device classification and/or the like. in one or more embodiments, search query may include source tables in which data should be retrieved from. In one or more embodiments, search query may include conditions and/or filters. For example, and without limitation, search query may include search conditions, such as minimum and maximum diameters, only cardiovascular devices belonging to a particular category and/or the like. In one or more embodiments, search query may include a plurality of nodes. A "node" as referred to herein refers to an element or entity within a data structure. A node in the context of database queries, also referred to as a 'query generation node' may refer to a step or action in the process of generating a query. For example, and without limitation, node may include a step of accessing a database of files, accessing a particular classification of files and the like. In one or more embodiments nodes may include steps such as, but not limited to receiving data identifying an initial set of data on database. In one or more embodiments, each node may represent a specific piece of information or condition related to the request. In one or more embodiments, nodes may be used to find and retrieve information within database. In one or more embodiments, nodes may be specific to what information should be retrieved. In one or more embodiments, nodes may include operations like table scans, index lookups, filtering conditions, and the like. In one or more embodiments, processor 110 may be configured to generate an SQL query and/or a search query including a plurality of nodes wherein each node may refer to a specific step in a process of data retrieval. In one or more embodiments, nodes may be used to filter information within database based on valve model datum. In one or more embodiments, nodes may provide instructions on how to identify and select the relevant data from database. In one or more embodiments, nodes may represent specific actions or conditions that need to be performed or met in order to retrieve the desired information from database. Each node may correspond to a specific element or event and may serve as a step in the process of generating a final query. In an embodiment, each node may be associated with a separate query, wherein each node may result in a different request received from database. In one or more embodiments, processor 110 may generate search query to query database to retrieve relevant information in association with valve model datum. In one or more embodiments, processor 110 may be configured to identify at least one available valve modem from a plurality of valve model as a function of the query and/or search query.

With continued reference to FIG. 1, in one or more embodiments, search query may include an annulus diameter. An "Annulus diameter" for the purposes of this disclosure refers to an internal diameter of a ring of the cardiovascular device that provides structural support to the heart valve. An annulus diameter may include a diameter of a valve annulus. In one or more embodiments, the valve annulus may include a ring that provides structural support to a heart valve. A proper sizing of the valve annulus ensures that there is no poor blood flow or leaks around the cardiovascular device. In one or more embodiments, the diameter may directly affect the flow of blood through the valve. An undersized valve may impede blood flow, while an oversized valve may lead to instability or other complications. In one or more embodiments, search query may include annulus diameter wherein annulus diameter may indicate the proper diameter of the valve annulus to be used on the patient. In one or more embodiments, aortic valves may include an annulus diameter ranging from 2.0 to 3.2 centimeters (cm). In one or more embodiments, a mitral valve may include an annulus diameter ranging from 2.7 to 3.5 cm. In one or more embodiments, a valve such as a tricuspid valve may include an annulus diameter of 2.8 cm to 3.6 cm. In one or more embodiments, annulus diameter may be determined using cardiac feature datum 138 and/or cardiovascular characteristic datum 150. Oinone or more embodiments, sizing of cardiovascular valves may determine the proper annulus diameter needed for the patient. In one or more embodiments, search query may include an annulus diameter indicating the proper diameter needed for a patient. In one or more embodiments, cardiac feature datum 138 and/or cardiovascular characteristic datum 150 may be used to determine the sizing of various anatomical structures and identify a corresponding annulus diameter. In one or more embodiments, search query may include annulus diameter wherein processor 110 may be configured to retrieve a 3D valve model that may be properly suited and/or sized for the patient. In one or more embodiments, cardiac feature datum 138 and/or cardiovascular characteristic datum 150 may be determined to identify the sizing of the annulus within an individual and the corresponding annulus diameter needed.

With continued reference to FIG. 1, memory 114 may contain instructions configuring processor 110 to generate a superimposed model 162 by superimposing at least a valve model 148 onto at least a 3D cardiac model 137. For the purposes of this disclosure, a "superimposed model" is a three-dimensional representation of a 3D Valve model superimposed onto at least a 3D cardiac model. As a non-limiting example, superimposed model 162 may include 3D representation of cardiovascular device 130 implanted within an artery of a patient's heart. For the purposes of this disclosure, "superimpose" is the process of overlaying an image onto another image. In some embodiments, processor 110 may be further configured to determine a superimpose position for superimposed model 162. For the purpose of this disclosure, a "superimpose position" is a position that a 3D Valve model can be superimposed on to a 3D cardiac model. As a non-limiting example, superimpose position may include a location of a cardiovascular device within 3D cardiac model 137. In an embodiment, superimpose position may include a position of superimposed model 162 in a field coordinate system. As a non-limiting example, superimpose position may be obtained using a machine vision system. As another non-limiting example, processor 110 may determine superimpose position as a function of cardiac feature datum 138, wherein the cardiac feature datum 138 may include a location of cardiovascular device within ultrasound image 104. In some embodiments, processor 110 may superimpose at least a valve model 148 onto at least a 3D cardiac model 137 as a function of superimpose position. In some embodiments, superimposed model 162 may be stored in a Cardio database 116. In some embodiments, superimposed model 162 may be retrieved from Cardio database 116.

With continued reference to FIG. 1, in some embodiments, superimposing at least a valve model 148 onto at least a 3D cardiac model 137 may include determining an optimal path 164 for a placement of the at least a 3D Valve model within the at least a 3D cardiac model 137, generating a path model 166 for the optimal path 164 and superimposing the path model 166 onto the at least a 3D cardiac model 137. For the purposes of this disclosure, an "optimal path" is a trajectory or route that minimizes risk and maximizes accuracy for the placement of the cardiovascular device within a heart. As a non-limiting example, optimal path 164 may include a path from the radial artery to the coronary artery. In some embodiments, optimal path 164 may be determined by evaluating anatomical constraints (cardiac feature datum 138 and/or cardiovascular characteristic datum 150), cardiovascular device specifications, and the like. In some embodiments, processor 110 may determine optimal path 164 using a graph-based pathfinding that represents 3D cardiac model 137 as a graph where nodes represent points in space and edges represent potential paths between them. As a non-limiting example, processor 110 may use Dijkstra's algorithm, A-star algorithm, and the like to determine optimal path 164. In some embodiments, user may manually generate optimal path 164. For example, and without limitation, user may manipulate user interface to generate optimal path 164.

With continued reference to FIG. 1, in some embodiments, processor 110 may determine optimal path 164 through the use of machine-learning module. In some embodiments, processor 110 may be configured to generate path training data. In a non-limiting example, path training data may include historical data from previous successful procedures of placement of cardiovascular devices. In another non-limiting example, path training data may include correlations between exemplary 3D cardiac models, exemplary 3D Valve models and exemplary optimal paths. In some embodiments, path training data may be stored in Cardio database 116. In some embodiments, path training data may be received from one or more users, Cardio database 116, external computing devices, and/or previous iterations of processing. As a non-limiting example, path training data may include instructions from a user, who may be an expert user, a past user in embodiments disclosed herein, or the like, which may be stored in memory and/or stored in Cardio database 116, where the instructions may include labeling of training examples. In some embodiments, path training data may be updated iteratively on a feedback loop. As a non-limiting example, processor 110 may update path training data iteratively through a feedback loop as a function of ultrasound image 104, 3D cardiac models, exemplary 3D Valve models, cardiac feature datum 138, image segment 142, or the like. In some embodiments, processor 110 may be configured to generate a path machine-learning model. In a non-limiting example, generating path machine-learning model may include training, retraining, or fine-tuning path machine-learning model using path training data or updated path training data. In some embodiments, processor 110 may be configured to determine optimal path 164 using path machine-learning model (i.e. trained or updated path machine-learning model). In some embodiments, generating training data and training machine-learning models may be simultaneous.

With continued reference to FIG. 1, for the purposes of this disclosure, a "path model" is a computational representation of an optimal path. In a non-limiting example, path model 166 may provide visual and numerical guidance for navigating the delivery system (catheter) and deploying cardiovascular device 130. As a non-limiting example, path model 166 may include trajectory representing a series of connected points, vectors, or curves defining cardiovascular device's path through a heart. In some embodiments, generating path model 166 may include dividing optimal path 164 into a series of path points. As a non-limiting example, path points may include start point that can be an entry point of a delivery system (e.g., the femoral vein, transseptal puncture site or septum fossa ovalis). As another non-limiting example, path points may include intermediate points that are points along the trajectory through cardiac structures such as the left atrium and right atrium. As another non-limiting example, path points may include end point that is a final position at the coronary artery where the cardiovascular device 130 will be deployed. In some embodiments, generating path model 166 may include annotating each path point with coordinates (e.g., [x, y, z] positions in 3D cardiac model 137) and orientation. In some embodiments, generating path model 166 may include interpolating optimal path using mathematical interpolation (e.g., cubic splines or Bézier curves) to connect path points. In one or more embodiments, path model 166 may be configured to provide visualization of implantation of the cardiovascular device within the patient's heart.

With continued reference to FIG. 1, memory 114 may contains instructions configuring processor 110 to display, using at least a display 108, at least 3D cardiac model and at least valve model. In one or more embodiments, memory 114 may contain instructions configuring processor to display a superimposed model 162. System 100 includes at least a display 108. For the purposes of this disclosure, a "display" is a device that presents visual information or data. As a non-limiting example, display 108 may present visual information or data in one or more forms of text, graphics, images, video, animation, and the like. Display 108 may be configured to provide a way for a user to view and/or interact with information, including but not limited to ultrasound image 104, 3D cardiac model 137, Valve model 148, superimposed model 162, and/or the like. In some embodiments, display 108 may be implemented in any user device 118 disclosed in the entirety of this disclosure. In some embodiments, display 108 may include different technologies, such as liquid crystal display (LCD), a light-emitting diode (LED), organic light-emitting diode (OLED), plasma, projection, touch screen, and/or the like. In some embodiments, display 108 may include varying resolutions, sizes, and aspect ratios.

With continued reference to FIG. 1, processor 110 may be configured to display 3D cardio model and the valve model. In one or more embodiments, display of valve model and 3D cardiac model may allow for a medical professional to identify placement of an already existing cardiovascular device and/or determine a placement for a new cardiovascular device. In one or more embodiments, processor 110 may be configured to display superimposed model 162 in order to provide visual aid to a medical professional. In one or more embodiments, visual aid may be provided during implantation of a cardiovascular device and/or during monitoring following implantation of the cardiovascular device.

With continued reference to FIG. 1, processor 110 may be configured to receive ultrasound image 104 and generate 3D cardiac model in order to aid in one or more valve repair procedures. In one or more embodiments, valve model datum may be used to identify an existing valve model within the patient and/or to identify a particular valve model that would be useful for implantation.

With continued reference to FIG. 1, in some embodiments, display 108 may include a plurality of display windows **168*a*-*b*. For the purposes of this disclosure, a "display window" is a defined visual area within a display. As a non-limiting example, display 108 may include a first display window 168*a*. In some embodiments, first display window 168*a* may be configured to display at least an ultrasound image 104, 3D cardiac model 137, and the like. In some embodiments, display 108 may include a second display window 168*b*. In some embodiments, second display window 168*b* may be configured to display superimposed model 162, path model 166**, and the like.

With continued reference to FIG. 1, in some embodiments, second display window **168*b* may include a user interface. For the purposes of this disclosure, a "user interface" is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof and the like. In some embodiments, user interface may operate on and/or be communicatively connected to a decentralized platform, metaverse, and/or a decentralized exchange platform associated with the user. For example, a user may interact with user interface in virtual reality. In some embodiments, a user may interact with the use interface using a computing device distinct from and communicatively connected to at least a processor 110**. For example, a smart phone, smart, tablet, or laptop operated by a user. In an embodiment, user interface may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

With continued reference to FIG. 1, in some embodiments, displaying at least a portion of at least a 3D cardiac model 137 and at least a 3D valve model 148 may include generating a pseudo TEE frame as a function of the at least a 3D cardiac model 137 and superimposing the at least a valve model 148 on to the pseudo TEE frame. For the purposes of this disclosure, a "pseudo transesophageal echocardiogram frame" is a two dimensional (2D) slice of a 3D cardiac model at a given view angle or position. In some embodiments, processor 110 may generate pseudo TEE frame by computationally projecting 3D cardiac model 137 onto a 2D plane using view labels or imaging parameters to replicate the perspective, depth, and anatomical detail in an actual TEE frame (ultrasound image 104). In some embodiments, pseudo TEE frame may include color Doppler overlays to simulate markers indicating optimal path or position datum. In some embodiments, processor 110 may display pseudo TEE frame through a display.

With continued reference to FIG. 1, additional disclosure related to generation of pseudo images (pseudo TEE frame) may be found in a number of co-owned patent applications listed below. Each of these applications are incorporated herein by reference in their entirety: U.S. Nonprovisional application Ser. No. 18/818,034, filed on Aug. 28, 2024, and entitled "APPARATUS AND METHODS FOR GENERATING A THREE-DIMENSIONAL (3D) MODEL OF AN ANATOMICAL OBJECT VIA MACHINE-LEARNING," which is a continuation-in-part of Non-provisional application Ser. No. 18/750,411 filed on Jun. 21, 2024, and entitled "APPARATUS AND METHODS FOR GENERATING A THREE-DIMENSIONAL (3D) MODEL OF AN ANATOMICAL OBJECT VIA MACHINE-LEARNING," which is a continuation of Non-provisional application Ser. No. 18/376,688 filed on Oct. 4, 2023, and entitled "APPARATUS AND METHODS FOR GENERATING A THREE-DIMENSIONAL (3D) MODEL OF CARDIAC ANATOMY VIA MACHINE-LEARNING," the entirety of which are incorporated herein by reference and U.S. Non-provisional application Ser. No. 18/817,870, filed on Aug. 28, 2024, and entitled "APPARATUS AND METHODS FOR SYNTHESIZING MEDICAL IMAGES," which is a continuation-in-part of Non-provisional application Ser. No. 18/509,520, filed on Nov. 15, 2023, and entitled "APPARATUS AND METHODS FOR SYNTHESIZING MEDICAL IMAGES," the entirety of which are incorporated herein by reference and U.S. Non-provisional application Ser. No. 18/818,152, filed on Aug. 28, 2024, and entitled "APPARATUS AND METHOD FOR GENERATING A THREE-DIMENSIONAL (3D) MODEL OF CARDIAC ANATOMY BASED ON MODEL UNCERTAINTY," which is a continuation-in-part of Non-provisional application Ser. No. 18/426,604, filed on Jan. 30, 2024, and entitled "APPARATUS AND METHOD FOR GENERATING A THREE-DIMENSIONAL (3D) MODEL OF CARDIAC ANATOMY BASED ON MODEL UNCERTAINTY," the entirety of which are incorporated herein by reference and U.S. Non-provisional application Ser. No. 18/818,311 filed on Aug. 28, 2024, and entitled "APPARATUS AND METHOD FOR GENERATING A THREE-DIMENSIONAL (3D) MODEL OF CARDIAC ANATOMY WITH AN OVERLAY," which is a continuation-in-part of Non-provisional application Ser. No. 18/395,087 filed on Dec. 22, 2023, and entitled "APPARATUS AND METHOD FOR GENERATING A THREE-DIMENSIONAL (3D) MODEL OF CARDIAC ANATOMY WITH AN OVERLAY," the entirety of which are incorporated herein by reference and U.S. Non-provisional application Ser. No. 18/648,176 filed on Apr. 26, 2024, and entitled "APPARATUS AND METHODS FOR VISUALIZATION WITHIN A THREE-DIMENSIONAL MODEL USING NEURAL NETWORKS," the entirety of which is incorporated herein by reference.

Referring now to FIG. 2, an exemplary display 200 used during planning of implantation of Cardiovascular device 130, according to some embodiments. In some embodiments, display 200 may be implemented in any user device 118. In some embodiments, display 200 may include a first display window **168*a* displaying at least an ultrasound image 104. In some embodiments, display 200 may include a second display window 168*b* displaying path model 166, 3D cardiac model 137, 3D Valve model 148, and the like. In some embodiments, user may interact with second display window 168*b* to manipulated with displayed models. In a non-limiting example, user may try placing different sizes and types of Cardiovascular device 130 on cardiovascular within 3D cardiac model 137**.

Figure 3:
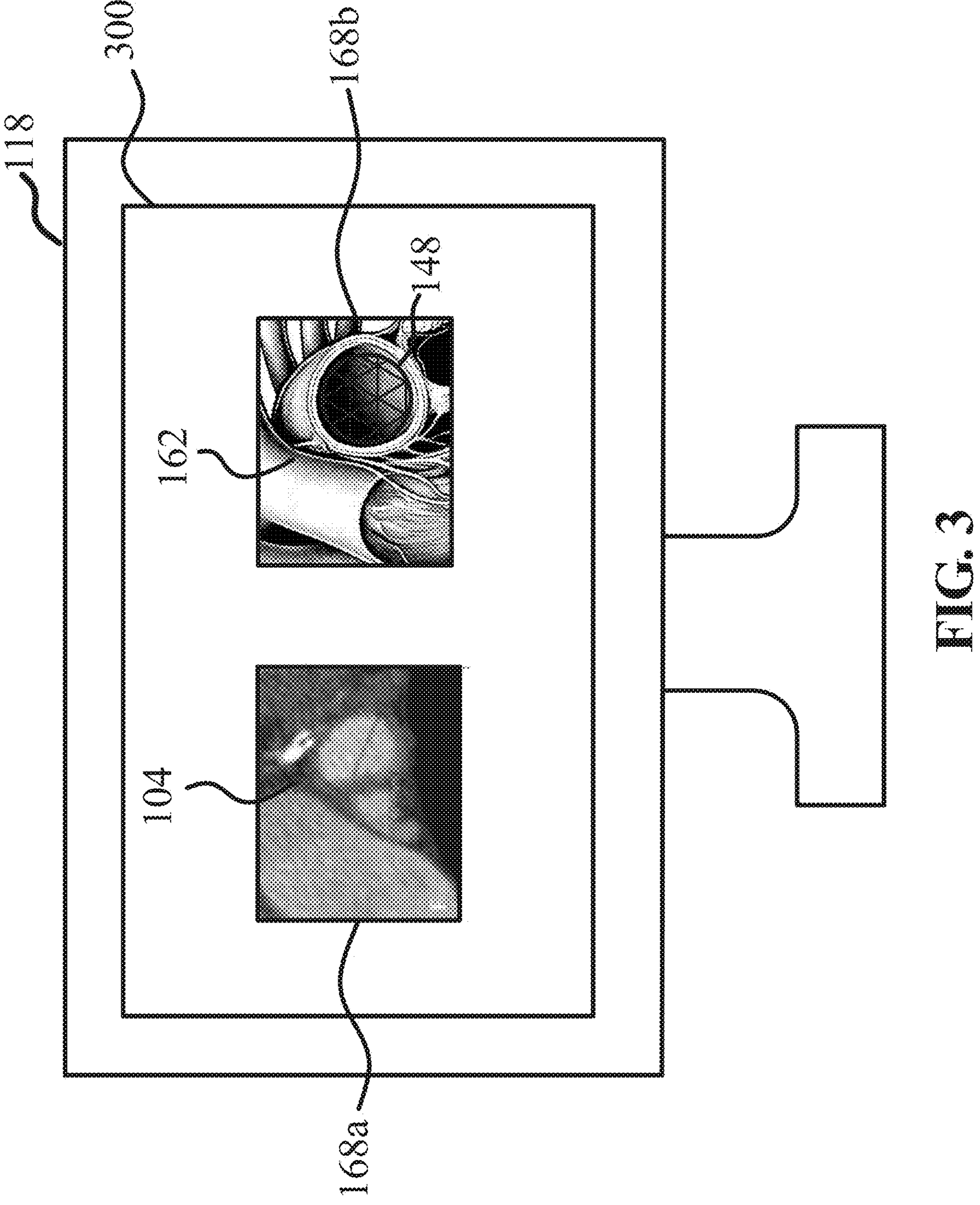
FIG. 3 illustrates an exemplary display used during implantation of cardiovascular device, according to some embodiments.

Referring now to FIG. 3, an exemplary display 300 used during planning of implantation of Cardiovascular device 130, according to some embodiments. In some embodiments, display 300 may be implemented in any user device 118. In some embodiments, display 300 may include a first display window **168*a* displaying at least an ultrasound image 104. In some embodiments, display 300 may include a second display window 168*b* displaying superimposed model 162, path model 166, 3D cardiac model 137, 3D Valve model 148, and the like. In a non-limiting example, second display window 168*b* may display a 3D cardiac model 137 with a 3D Valve model 148 superimposed on to the 3D cardiac model 137 (superimposed model 162). In some embodiments, user may interact with second display window 168*b* to manipulated with displayed models. In a non-limiting example, user may be placing Cardiovascular device 130 within an artery or valve of a patient's heart with a guide (superimposed model 162, path model 166, and the like) displayed on a display 300**.

Figure 4:
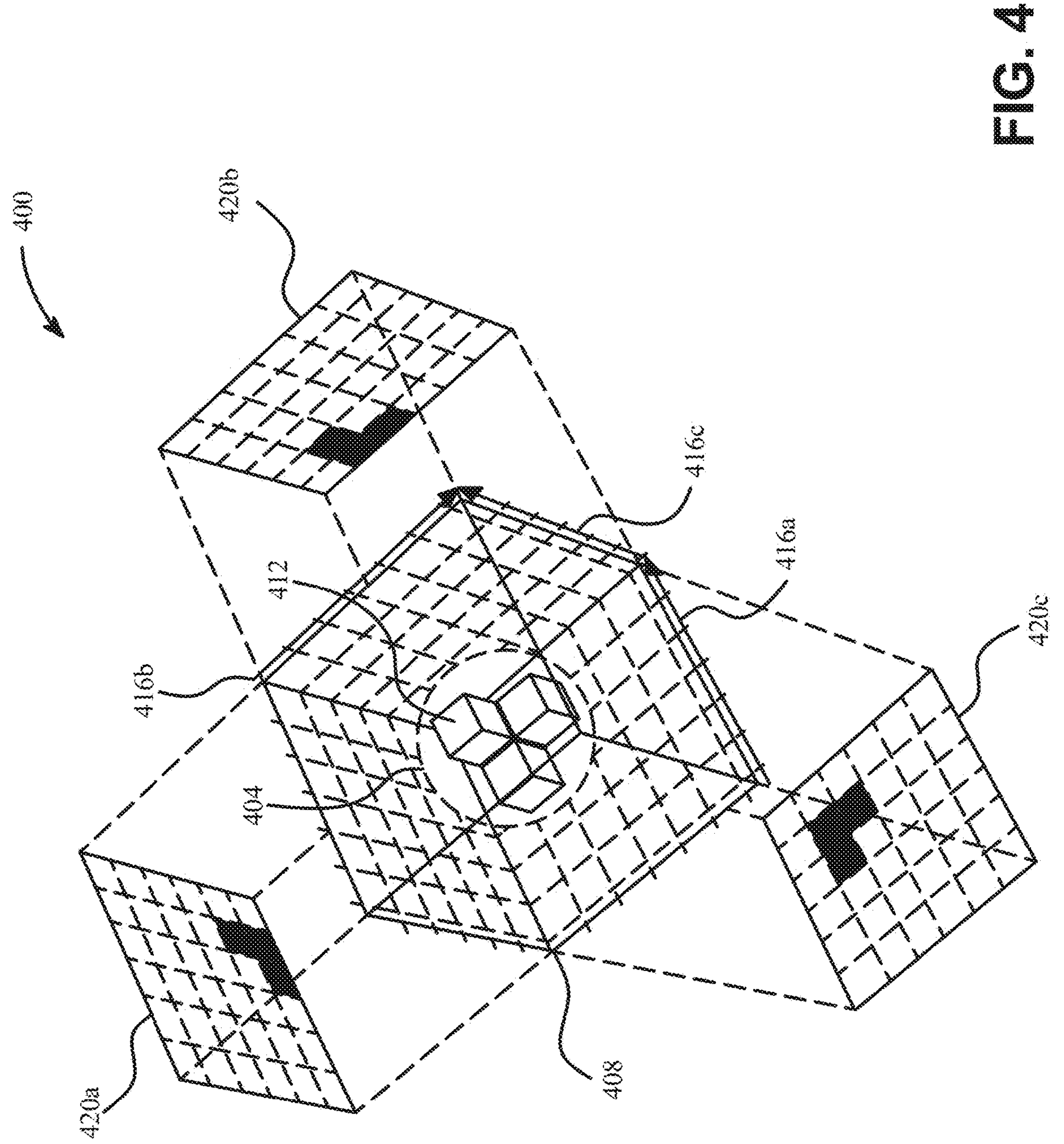
FIG. 4 illustrates an exemplary embodiment of a three-dimensional (3D) voxel occupancy representation.

Now referring to FIG. 4, an exemplary embodiment of a 3D VOR 400 is illustrated. 3D VOR 400 may be used to represent 3D object 404. In an embodiment, 3D VOR 400 may divide a 3D space 408 into a grid of one or more cubic units e.g., voxels 412, wherein each voxel 412 represents a specific volume within 3D space 408. In a non-limiting example, 3D object 404 may include a structure pertaining to a subject.

Still referring to FIG. 4, in some cases, each voxel 412 may act as a basic building block. In a non-limiting example, each voxel 412 may be configured to represent a discrete portion of 3D space 408. In an embodiment, each voxel 412 may include a presence indicator as described above with reference to FIG. 1, which denotes whether the voxel is occupied or unoccupied. In such embodiment, the binary or continuous value may allow 3D VOR 400 to map the presence or absence of material within each voxel 412, creating a granular representation of 3D object 404.

With continued reference to FIG. 4, in some cases, the resolution of 3D VOR 400 may be determined by the size and number of voxels within the grid. In a non-limiting example, smaller voxel may provide a higher resolution, capturing finer details, while larger voxels offer a more generalized representation.

Still referring to FIG. 4, in an embodiment, voxels 412 may be arranged in a regular pattern along three axis 416*a-c*, each pointing a distinct direction. In a non-limiting example, voxels 412 may be arranged along x, y, and z axes, wherein such arrangement may facilitate efficient manipulation and rendering of the 3D object 404. In some cases, cardiac feature datums 420*a-c* such as, without limitation, edges, surfaces, textures, and any other cardiac feature datums as described above with reference to FIG. 1, may be extracted from 3D VOR 400 by analyzing the relationships and patterns between neighboring voxels.

Figure 5:
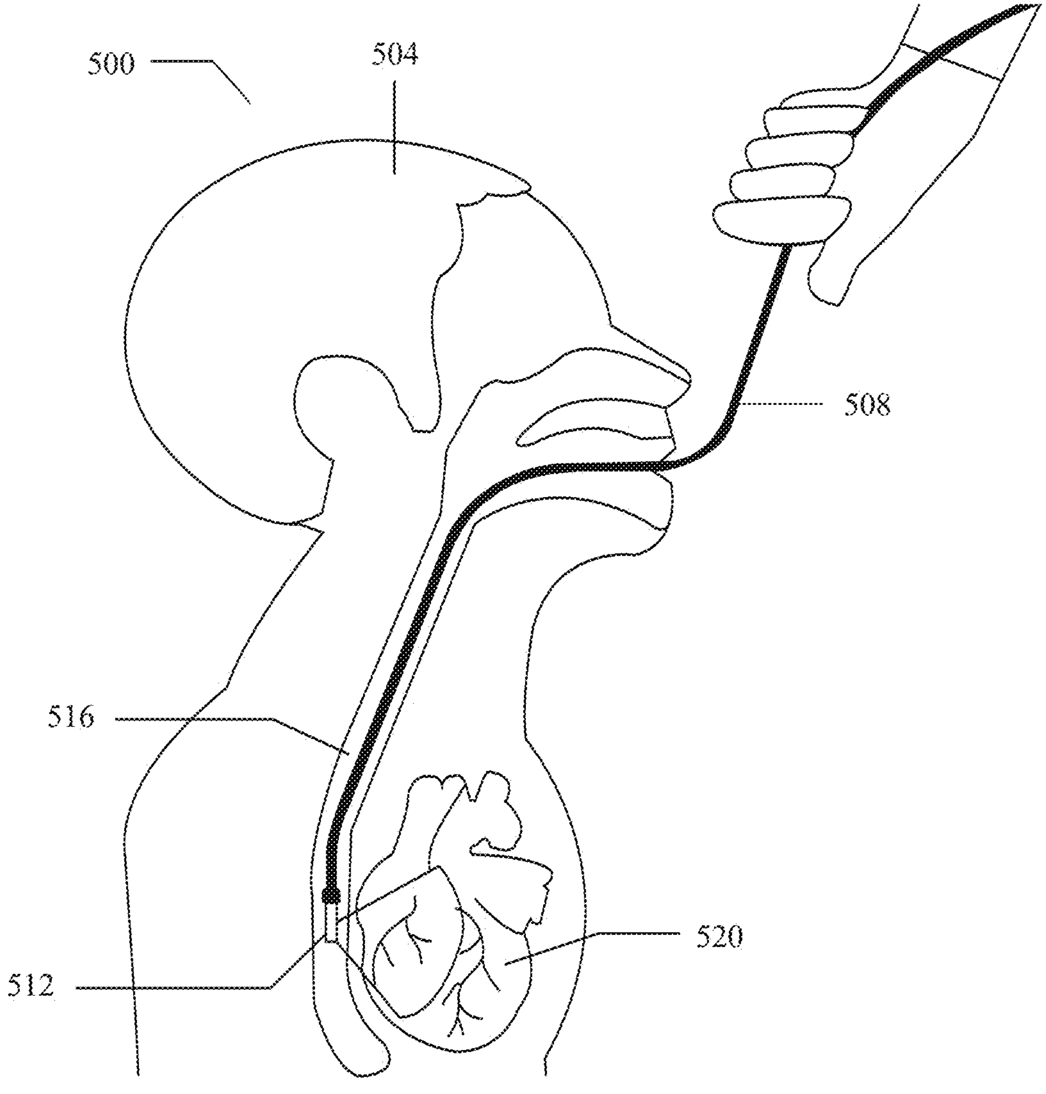
FIG. 5 illustrates a schematic diagram of an exemplary transesophageal echocardiogram.

Now referring to FIG. 5, a schematic of an exemplary transesophageal echocardiogram (TEE) procedure 500 is shown. In some cases, TEE procedure 500 may be performed during another procedure for instance heart surgery. According to some embodiments, a patient 504 has an endoscope 508, with an ultrasonic transducer 512, inserted into his esophagus 516. As one's esophagus 516 is proximal one's heart 520, ultrasonic transducer 512 may generate echocardiograms.

Still referring to FIG. 5, in some embodiments, transesophageal echocardiography (TEE) may provide superior imaging quality than intracardiac echocardiography (ICE), as larger ultrasound transducers 512 may be placed within the esophagus 516 than within heart 520. In some cases, ultrasound transducers may be substantially miniaturized to fit within heart 520, as in ICE catheters. As esophagus 516 may be proximal to heart 520, TEE may provide a clear image of various heart structures without needing vascular access (as commonly required by ICE). Additionally, TEE may be performed without obstructing patient's 504 ribcage and intermediary tissues (as commonly required by transthoracic echocardiography [TTE]). In some cases, TEE images may also provide information associated with angle of acquisition. Angle of acquisition may be an angle of TEE probe with respect to esophagus 516 (e.g., esophageal axis).

Still referring to FIG. 5, in some embodiments, TEE echocardiogram data, including images showing heart structures and, in some cases, angle of acquisition, may be used as input to any machine learning process described in this application, for instance with reference to FIGS. 1-4 and 6-13. For instance TEE echocardiogram data may be used to reconstruct 3D heart models. In some cases, TEE echocardiogram data may be input into a machine learning model that outputs a 3D heart model (e.g., 3D mesh model and/or statistical shape model).

Still referring to FIG. 5, in some embodiments, TEE may be a preferred imaging modality for structural heart interventions, such as without limitation left atrial appendage occlusion (LAOO), a stent, or a valve. In some cases, technology and improvements described in this disclosure permit creation and/or modification of a 3D heart mesh from TEE data to aid in planning implant size selection, as well as to guide implantation procedures. In some cases, virtual placement of a 3D model of a candidate implant (such as without limitation LAAO device) can be simulated on a 3D heart model generated by any method described in this disclosure. This novel and improved functionality may validate appropriate size and placement of implants within heart 520, as well as other organs within body of patient 504. For example, in the context of electrophysiology procedures, TEE procedure 500 can be used to create heart anatomical models that can be used as reference for electroanatomic mapping, and guidance of ablation catheters for atrial fibrillation treatment procedures (such as without limitation puncturing septum for Cardiovascular device placement).

Still referring to FIG. 5, in some embodiments, applications described with reference to TEE procedure 500 above can be extended for use with TTE and point of care ultrasound (POCUS). In some cases, both TTE and POCUS may acquire ultrasound images of chest/surface of patient 504. In some cases, TTE and POCUS data may be used as an input (and/or training data) for any machine learning process described in this disclosure, for instance with reference to FIGS. 1-4 and 6-13. In some cases, use of TTE and/or POCUS data (in machine learning processes described in this disclosure) may require adjustment in ultrasound acquisition parameters and positions to acquire a sufficient number of frames for 3D reconstruction. In some cases, TTE and POCUS may offer improved accessibility (with POCUS being portable/mobile as well) and non-invasive 3D heart modeling, often without anesthesia or sedation, compared to catheterized 3D heart modeling commonly performed today for electroanatomical mapping and ablation procedures.

Figure 6:
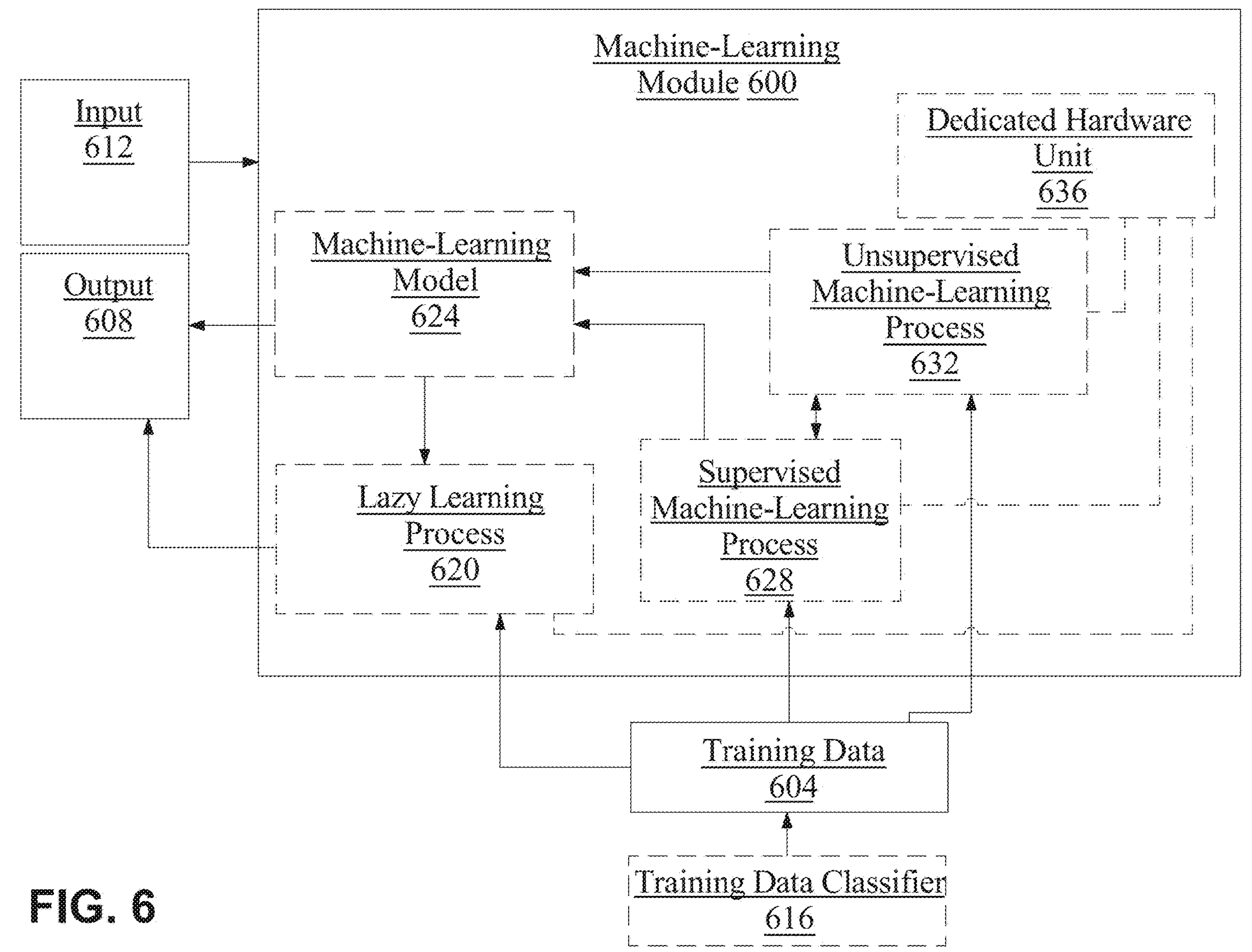
FIG. 6 illustrates a block diagram of an exemplary embodiment of a machine learning model.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm instantiated in hardware or software logic, data structures, and/or functions that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example, input data may include ultrasound image 104, 3D cardiac model 137, 3D Valve model 148, TEE angle datum 120, cardiac feature datum 138, 3D point cloud 140, cardiovascular characteristic datum 150, optimal path 164, device IFU data 126, and the like. As a non-limiting illustrative example, output data may include 3D cardiac model 137, 3D Valve model 148, TEE angle datum 120, cardiac feature datum 138, 3D point cloud 140, cardiovascular characteristic datum 150, optimal path 164, superimposed model 162, valve model datum 128, pass datum 160, path model 166, view label 136, image inquiry datum 124, and the like.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to a patient cohort related to patient's age, gender, medical experience, medical record, and the like.

Still referring to FIG. 6, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 6, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 6, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 6, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 6, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 6, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 6, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 6, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 6, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 6, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 6, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 6, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include ultrasound image 104, 3D cardiac model 137, 3D Valve model 148, TEE angle datum 120, cardiac feature datum 138, 3D point cloud 140, cardiovascular characteristic datum 150, optimal path 164, device IFU data 126, and the like as described above as inputs, 3D cardiac model 137, 3D Valve model 148, TEE angle datum 120, cardiac feature datum 138, 3D point cloud 140, cardiovascular characteristic datum 150, optimal path 164, superimposed model 162, valve model datum 128, pass datum 160, path model 166, view label 136, image inquiry datum 124, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

With further reference to FIG. 6, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 6, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 632 may not require a response variable; unsupervised processes 632 may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the clastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 6, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0"

voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 6, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 6, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 6, one or more processes or algorithms described above may be performed by at least a dedicated hardware unit 636. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 636 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 636 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 636 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 7:
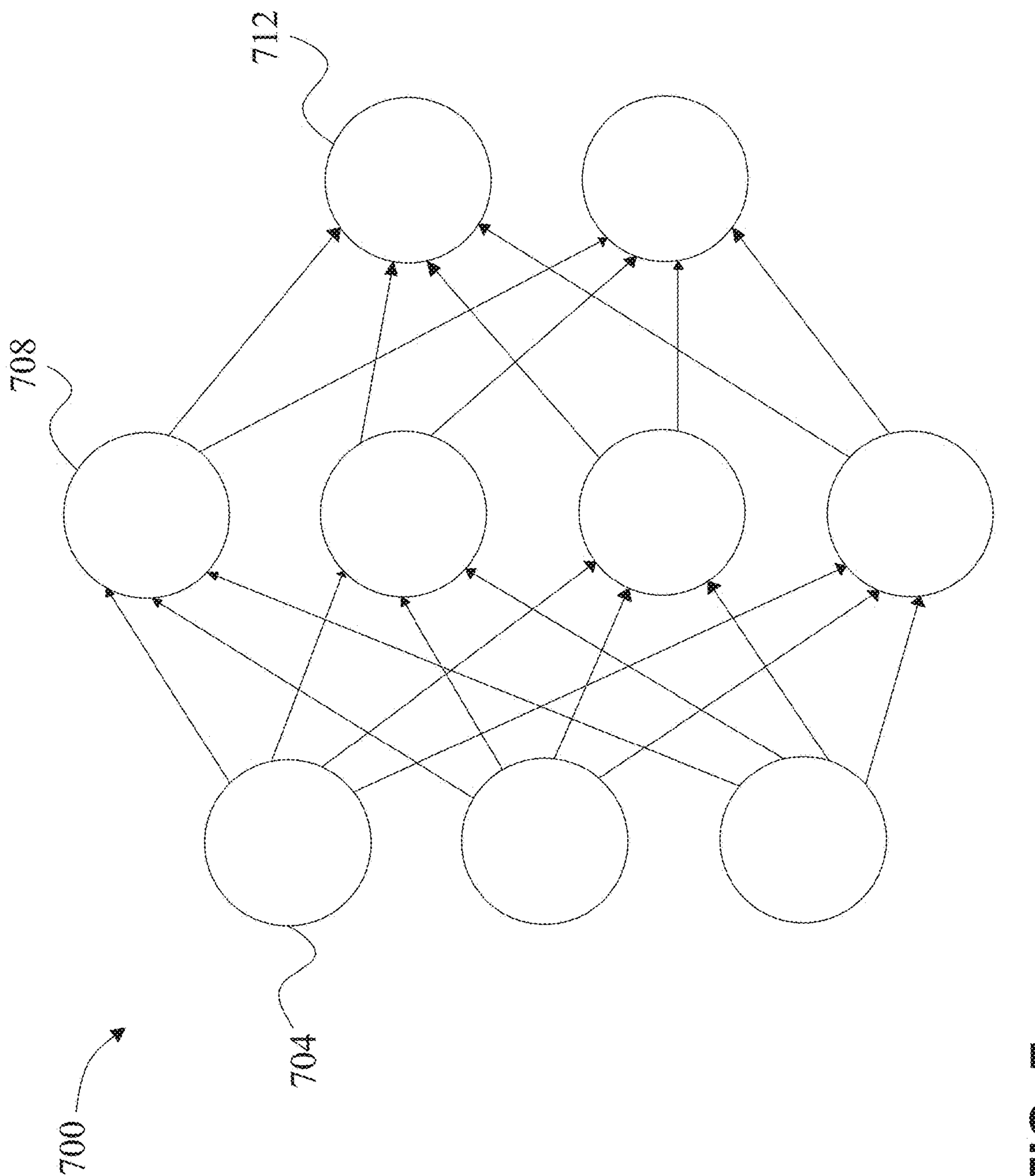
FIG. 7 illustrates a schematic diagram of an exemplary embodiment of a neural network.

Referring now to FIG. 7, an exemplary embodiment of neural network 700 is illustrated. A neural network 700 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 8:
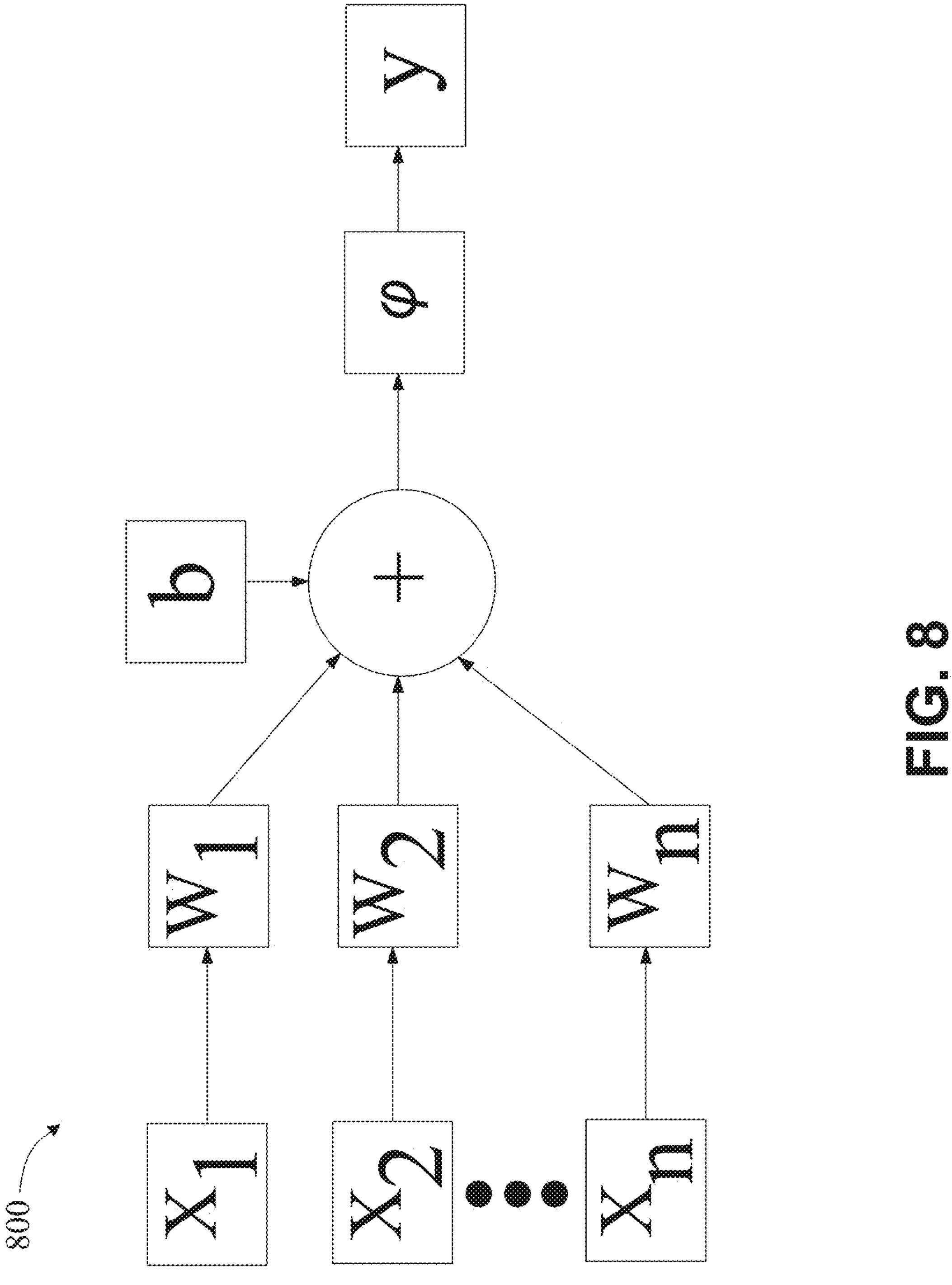
FIG. 8 illustrates a schematic diagram of an exemplary embodiment of a neural network node.

Referring now to FIG. 8, an exemplary embodiment of a node 800 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(\alpha x, x)$ for some $\alpha$, an exponential linear units function such as $$f(x) = \begin{cases} x \text{ for } x \geq 0 \\ \alpha(e^x - 1) \text{ for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=\alpha(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 9:
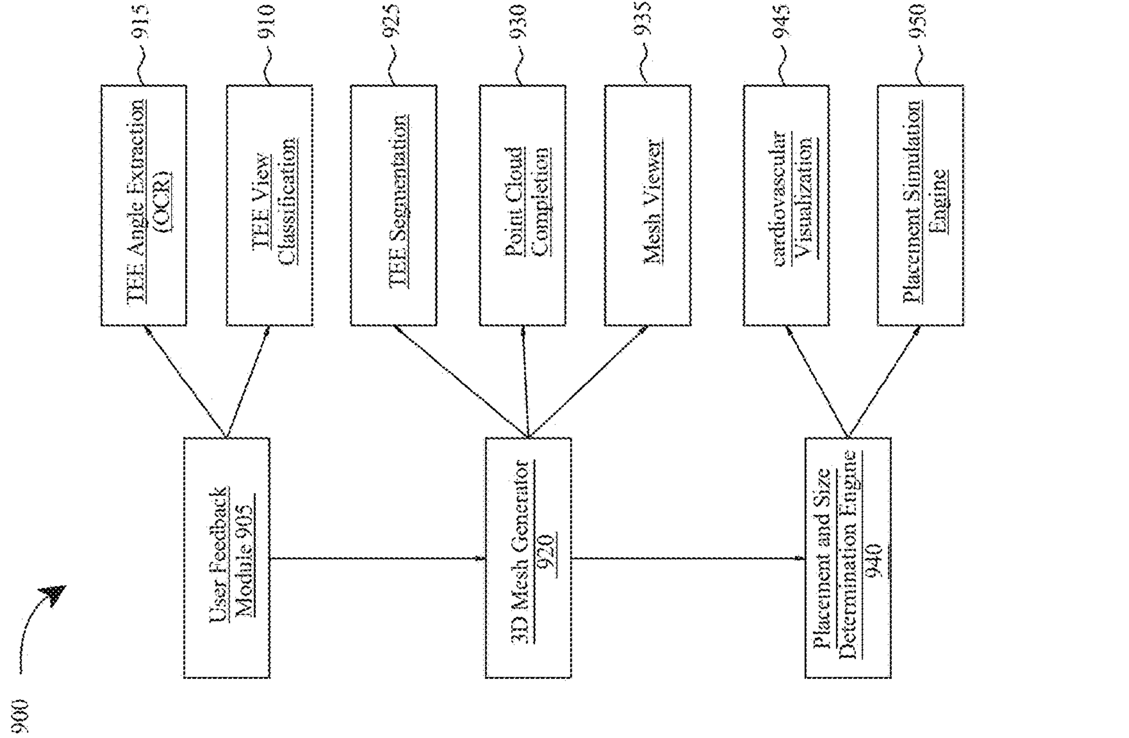
FIG. 9 illustrates a flow diagram showing an exemplary planning method.

Referring now to FIG. 9, a flow diagram showing an exemplary planning method 900 is illustrated. In some embodiments, systems and methods described in this disclosure may be used for planning of implantation of Cardiovascular device 130. In some embodiments, planning method 900 may include a user feedback module 905 that provides feedback to an operator (user) to ensure that TEE sensor (ultrasound sensor 106) position and orientation has captured frames and views (ultrasound image 104) that are in sync with Watchman IFU (device IFU data 126). Planning method 900 may be implemented by one or more of following components: first component 910, TEE view classification engine and second component 915, TEE angle extraction to capture TEE sensor angle (TEE angle datum 120) rendered on ultrasound frames. In some embodiments, once necessary and sufficient TEE frame views have been captured, the next phase of the planning method 900 may implement a 3D mesh generator 920 that generates a 3D mesh (3D mesh model 144) of arteries and/or valves of a patient's heart based on the captured TEE frames. In some embodiments, planning method 900 may be further implemented by one or more of the following components: third component 925, TEE segmentation module, fourth component 930, point cloud completion to generate the 3D mesh and fifth component 935, mesh viewer. In some embodiments, once the 3D mesh is generated, the next phase of the planning method 900 may implement a placement and size determination engine 940 that helps the user determine lock in on a particular cardiovascular device and placement (position and orientation), which may be implemented by the following components: sixth component 945, cardiovascular visualization including simulation of recommended device compression (compression rate 152), and the like, seventh component 950, placement simulation engine that tries out many placements and estimates a "placement objective function" and can recommends the top placements (valve model datum 128, optimal path 164, and the like) to the user.

Figure 10:
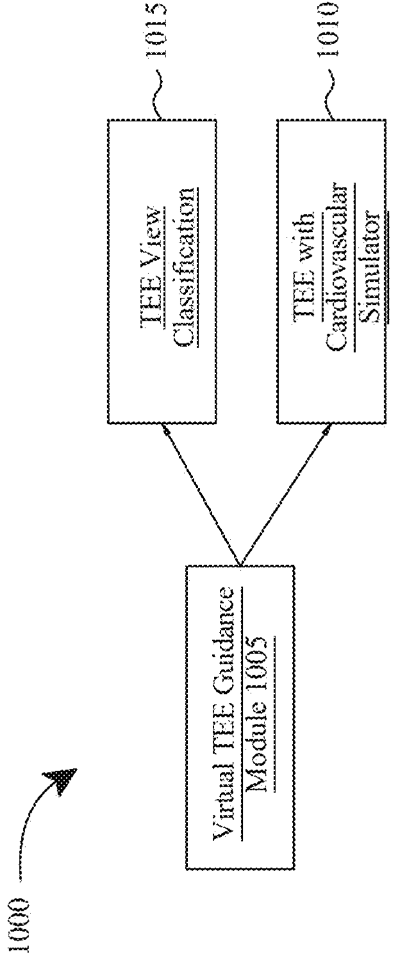
FIG. 10 illustrates a flow diagram showing an exemplary implantation method.

Referring now to FIG. 10, a flow diagram showing an exemplary implantation method 1000 is illustrated. In some embodiments, systems and methods described in this disclosure may be used for implantation of Cardiovascular device 130. Implantation method 1000 can help a user to execute a recommended placement. In some embodiments, next to a real-time Passthrough Ultrasound viewer (first display window 168*a*), an Anumana Implantation Helper window (second display window 168*b*) may render a view of a TEE ultrasound frame (ultrasound image 104) with a recommended cardiovascular device (valve model datum 128) at a recommended placement. The Anumana Implantation Helper window view may be calculated by reading off (using OCR 122) the angle (TEE angle datum 120) displayed in the TEE ultrasound frame and then simulating the TEE frame, with the valve model (valve model 148) placed at the recommended position. For this calculation, the TEE sensor may be assumed to be at a designated position. In some embodiments, implantation method 1000 may be aided by the following components of a virtual TEE guidance module 1005: first component 1010, TEE with cardiovascular simulator that generates a TEE frame based on angle and includes the cardiovascular device visualization placed at the recommended placement and second component 1015, TEE view classification engine (view classifier 134) for TEE frame with dynamic catheter and opened Watchman.

Figure 11:
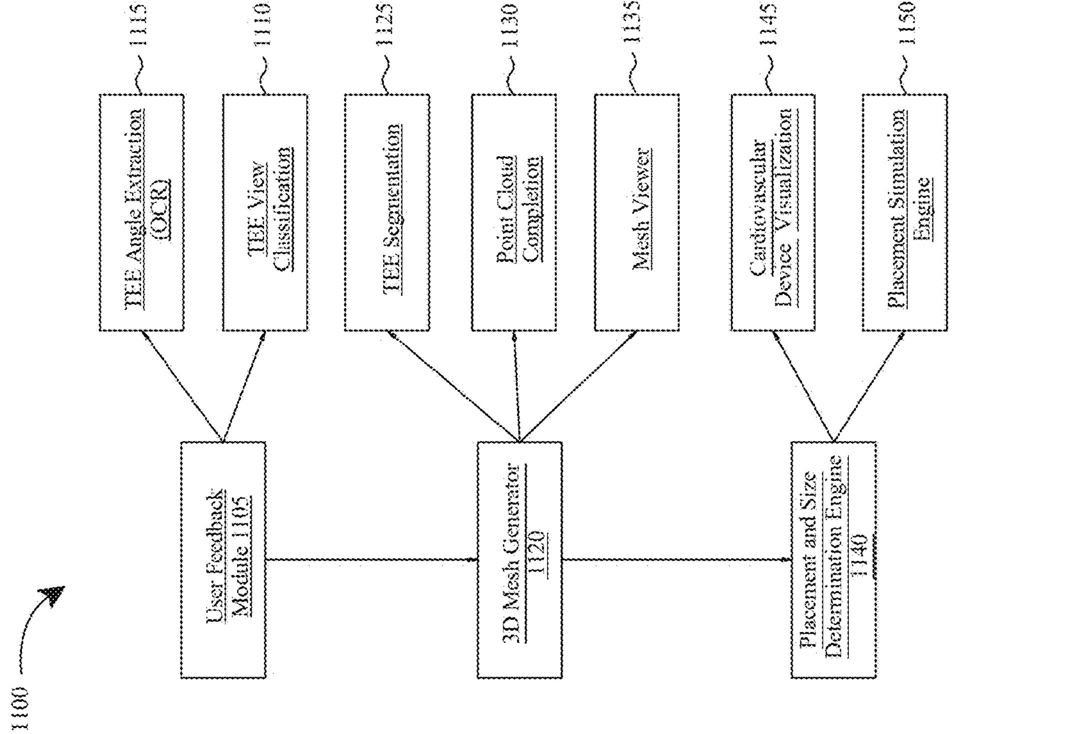
FIG. 11 illustrates a flow diagram showing an exemplary post-implantation method.

Referring now to FIG. 11, a flow diagram showing an exemplary post-implantation method 1100 is illustrated. In some embodiments, post-implantation method 1100 may include much of the same functionality as planning method 900, described in this disclosure. Post-implantation method 1100 may also include actual cardiovascular deice placement, overlaid on recommended valve model placement. Components that implement post-implantation method 1100 may be same as components described with respect to FIG. 9 while the components may be expected to work with the actual cardiovascular device at its actual placement. For example, and without limitation, post-implantation method 1100 may be implemented by one or more of following components of following modules: user feedback module 1105 with first component 1110, TEE view classification and second component 1115, TEE angle extraction, 3D mesh generator 1120 with third component 1125, TEE segmentation, fourth component 1130, point cloud completion and fifth component 1135, mesh viewer, and placement and size determination engine 1140 with sixth component 1145, cardiovascular device visualization and seventh component 1150, placement simulation engine. in one or more embodiments, sixth component 1145 and/or seventh component 1150 may be used to verify whether a device, such as cardiovascular device has been implanted correctly. In one or more embodiments, post implantation method 110 may be used to verify a correct placement of a cardiovascular device following implantation. In one or more embodiments, placement simulation engine may simulate proper placement of a cardiovascular device, wherein placement simulation engine may also be used to ensure proper placement of the cardiovascular device.

Figure 12:
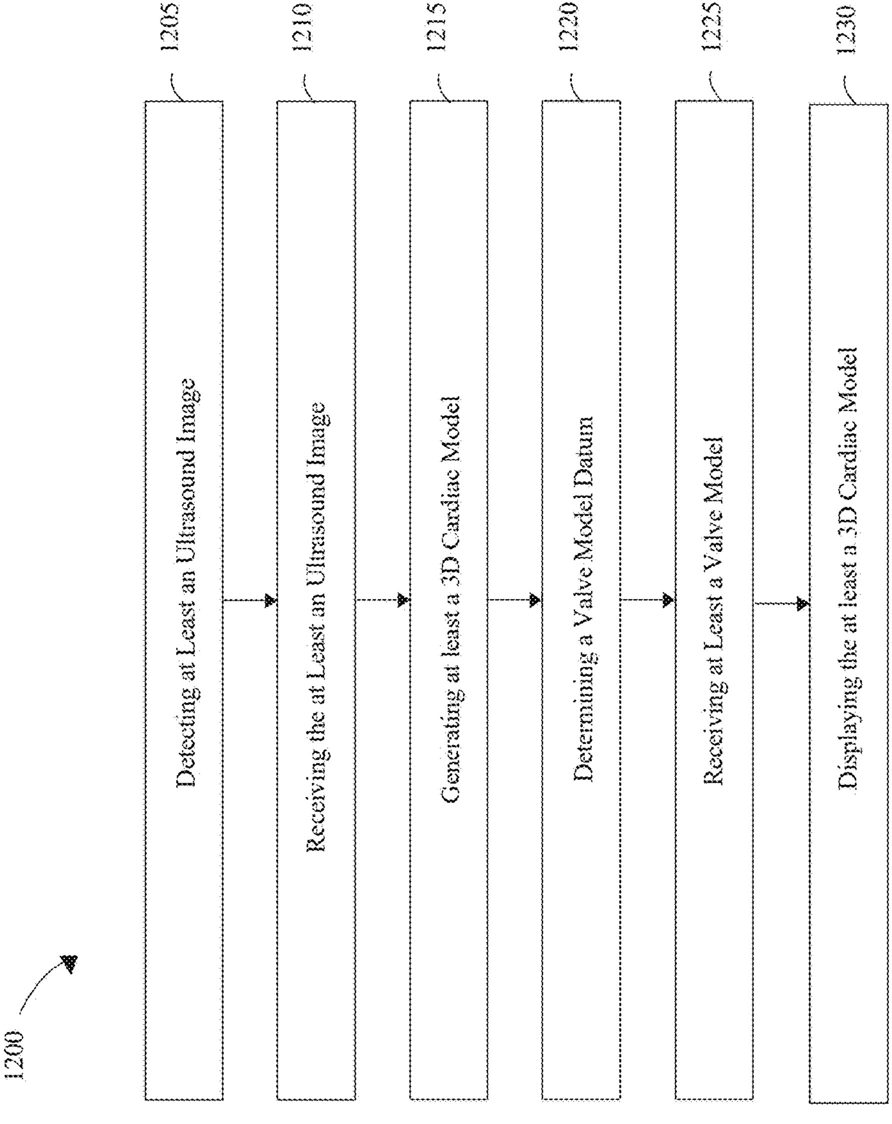
FIG. 12 illustrates a flow diagram of an exemplary method for transesophageal echocardiogram-guided implantation of a valve device.

Referring now to FIG. 12, a method 1200 for transesophageal echocardiogram-guided implantation of a valve device is described. At step 1205, method 1200 includes detecting, by at least a transesophageal echocardiogram system, at least an ultrasound image, wherein the at least a transesophageal echocardiogram system includes at least an ultrasound sensor configured to be located within an esophagus of a patient and detect the at least an ultrasound image as a function of cardiac tissue of the patient.

With continued reference to FIG. 12, at step 1210 method 1200 includes receiving, by at least a computing device, the at least an ultrasound image.

With continued reference to FIG. 12, at step 1215 method 1200 includes generating, by the at least a computing device, at least a 3D cardiac model representative of a heart of the patient as a function of the at least an ultrasound image wherein the at least an ultrasound image includes a two-dimensional image of the heart of the patient. In some embodiments, the 3D cardiac model may include a three dimensional interpolation of the two-dimensional image. In one or more embodiments, generating, by the at least a computing device, the at least a 3D cardiac model includes extracting at least a cardiac feature from the at least an ultrasound image and segmenting the at least an ultrasound image into a plurality of image segments as a function of the at least a cardiac feature. In one or more embodiments, generating, by the at least a computing device, the at least a 3D cardiac model representative of the heart of the patient includes receiving a generic 3D model, identifying one or more anomalies within the at least an ultrasound image and generating the at least a 3D cardiac model as a function of the generic 3D model and the one or more anomalies. In one or more embodiments, at least one anomaly of the one or more anomalies includes a spatial distortion of at least one cardiac feature.

With continued reference to FIG. 12, at step 1220 method 1200 includes determining, by the at least a computing device, a valve model datum as a function of the 3D cardiac model.

With continued reference to FIG. 12, at step 1225 method 1200 includes receiving, by the at least a computing device, at least valve model representative of at least a cardiovascular device to be placed within the patient as a function of the valve model datum. In one or more embodiments, the cardiovascular device includes a heart valve. In one or more embodiments, the valve model datum includes information associated with a dimension of the cardiovascular device. In one or more embodiments, wherein receiving, by the at least a computing device, the at least valve model representative of the at least a cardiovascular device to be placed within the patient includes generating a search query for a device database as a function of the valve model datum, wherein the device database includes a plurality of valve models representative of a plurality of cardiovascular devices and identifying at least one available valve model from the plurality of valve models as a function of the search query. In one or more embodiments, the search query includes an annulus diameter.

With continued reference to FIG. 12, at step 1230 method 1200 includes displaying, by the at least a computing device, the at least a 3D cardiac model and the at least a valve model. In one or more embodiments, displaying, by the at least a computing device, the at least a 3D cardiac model and the at least valve model includes superimposing the at least a valve model onto to the 3D cardiac model to create a superimposed model and displaying the superimposed model. In one or more embodiments, displaying the superimposed model further includes displaying a path model for implantation of the cardiovascular device within the heart of the patient. In one or more embodiments, displaying, by the at least a computing device, the at least a 3D cardiac model and the at least a valve model includes generating a pseudo TEE frame as a function of the at least a 3D cardiac model and a view label and superimposing the at least a valve model on to the pseudo TEE frame.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
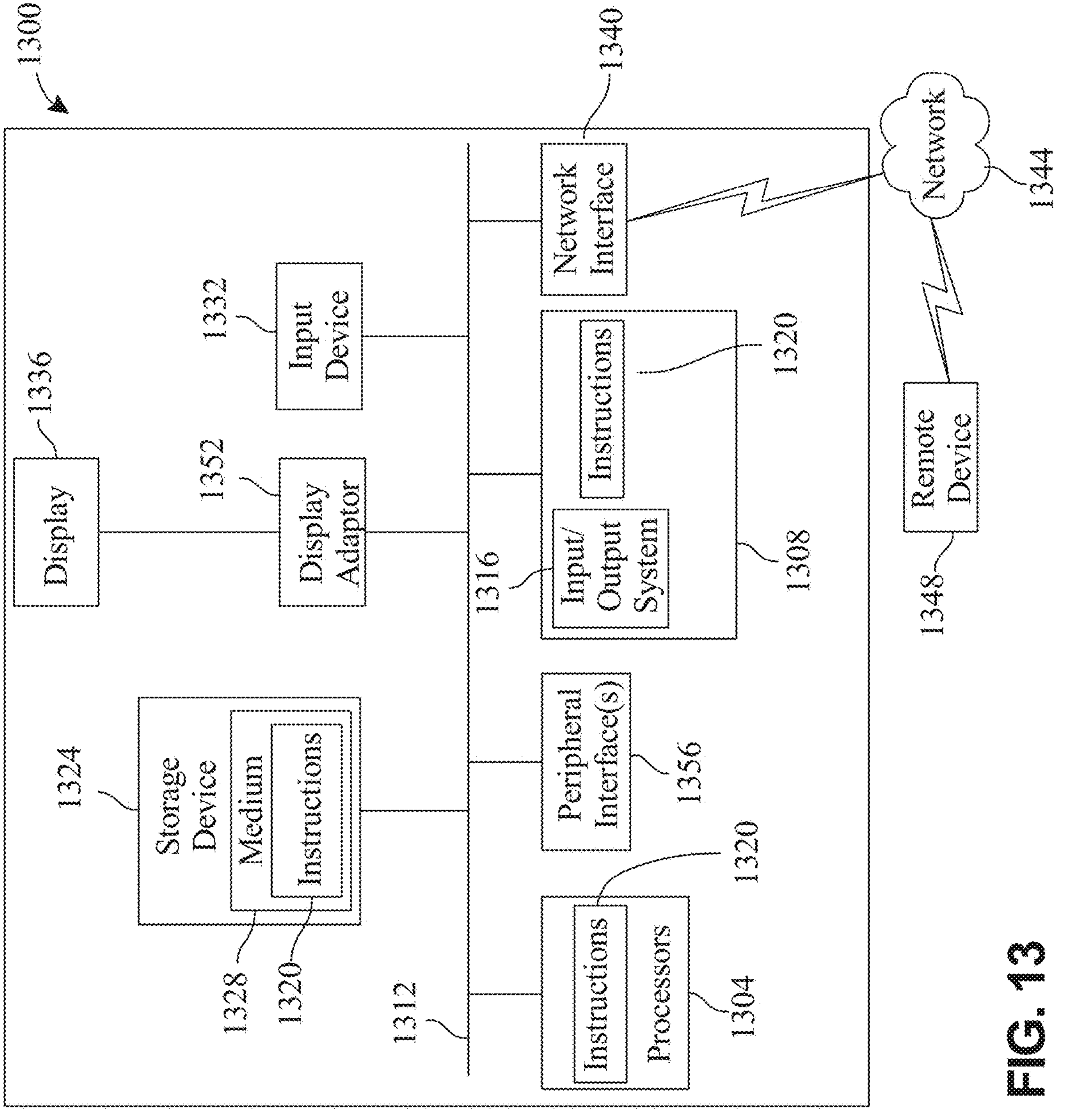
FIG. 13 illustrates a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display 1336. Examples of a display device include, but are not limited to, a liquid crystal display (LCD), a cathode ray tube (CRT), a plasma display, a light emitting diode (LED) display, and any combinations thereof. Display adapter 1352 and display 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for transesophageal echocardiogram-guided implantation of a valve device, the system comprising:

at least a transesophageal echocardiogram system comprising at least an ultrasound sensor configured to be located within an esophagus of a patient and detect at least an ultrasound image as a function of cardiac tissue of the patient; and at least a computing device configured to:

receive the at least an ultrasound image;

generate at least a three-dimensional (3D) cardiac model representative of a heart of the patient as a function of the at least an ultrasound image, wherein the at least an ultrasound image comprises a two-dimensional image of the heart of the patient, wherein generating the at least a 3D cardiac model comprises:

identifying one or more anomalies within the at least an ultrasound image; and generating the at least a 3D cardiac model as a function of the one or more anomalies by modifying one or more voxels within a generic 3D model;

determine a valve model datum as a function of the 3D cardiac model;

receive at least a valve model representative of at least a cardiovascular device to be placed within the patient as a function of the valve model datum;

generate at least a recommended cardiovascular device placement; and display the at least a 3D cardiac model and the at least a valve model, wherein displaying the at least a 3D cardiac model and the at least a valve model comprises displaying an actual cardiovascular device placement overlaid on the recommended cardiovascular device placement.

2. The system of claim 1, wherein displaying the at least a 3D cardiac model and the at least a valve model comprises:

generating a pseudo transesophageal echocardiogram (TEE) frame as a function of the at least a 3D cardiac model and a view label; and superimposing the at least a valve model on to the pseudo TEE frame.

3. The system of claim 1, wherein the valve model datum comprises information associated with a dimension of the cardiovascular device.

4. The system of claim 1, wherein displaying the at least a 3D cardiac model and the at least valve model comprises:

superimposing the at least a valve model onto to the 3D cardiac model to create a superimposed model; and displaying the superimposed model.

5. The system of claim 4, wherein displaying the superimposed model further comprises displaying a path model for implantation of the cardiovascular device within the heart of the patient.

6. The system of claim 1, wherein generating the at least a 3D cardiac model comprises:

extracting at least a cardiac feature from the at least an ultrasound image; and segmenting the at least an ultrasound image into a plurality of image segments as a function of the at least a cardiac feature.

7. The system of claim 1, wherein generating the at least a 3D cardiac model representative of the heart of the patient comprises:

receiving the generic 3D model; and generating the at least a 3D cardiac model using a statistical shape model.

8. The system of claim 7, wherein at least one anomaly of the one or more anomalies comprises a spatial distortion of at least one cardiac feature.

9. The system of claim 1, wherein receiving the at least valve model representative of the at least a cardiovascular device to be placed within the patient comprises:

generating a search query for a device database as a function of the valve model datum, wherein the device database comprises a plurality of valve models representative of a plurality of cardiovascular devices; and identifying at least one available valve model from the plurality of valve models as a function of the search query.

10. The system of claim 9, wherein the search query comprises an annulus diameter associated with the valve model.

11. The system of claim 1, wherein generating the at least a 3D cardiac model comprises generating the at least a 3D cardiac model using a point completion model.

12. A method for transesophageal echocardiogram-guided implantation of a valve device, the method comprising:

detecting, by at least a transesophageal echocardiogram system, at least an ultrasound image, wherein the at least a transesophageal echocardiogram system comprises at least an ultrasound sensor configured to be located within an esophagus of a patient and detect the at least an ultrasound image as a function of cardiac tissue of the patient;

receiving, by at least a computing device, the at least an ultrasound image;

generating, by the at least a computing device, at least a three-dimensional (3D) cardiac model representative of a heart of the patient as a function of the at least an ultrasound image, wherein the at least an ultrasound image comprises a two-dimensional image of the heart of the patient, wherein generating the at least a 3D cardiac model comprises:

identifying one or more anomalies within the at least an ultrasound image; and generating the at least a 3D cardiac model as a function of the one or more anomalies by modifying one or more voxels within a generic 3D model;

determining, by the at least a computing device, a valve model datum as a function of the 3D cardiac model;

receiving, by the at least a computing device, at least a valve model representative of at least a cardiovascular device to be placed within the patient as a function of the valve model datum;

generating at least a recommended cardiovascular device placement; and displaying, by the at least a computing device, the at least a 3D cardiac model and the at least a valve model, wherein displaying the at least a 3D cardiac model and the at least a valve model comprises displaying an actual cardiovascular device placement overlaid on the recommended cardiovascular device placement.

13. The method of claim 12, wherein displaying, by the at least a computing device, the at least a 3D cardiac model and the at least a valve model comprises:

generating a pseudo transesophageal echocardiogram (TEE) frame as a function of the at least a 3D cardiac model and a view label; and superimposing the at least a valve model on to the pseudo TEE frame.

14. The method of claim 12, wherein the valve model datum comprises information associated with a dimension of the cardiovascular device.

15. The method of claim 12, wherein displaying, by the at least a computing device, the at least a 3D cardiac model and the at least valve model comprises:

superimposing the at least a valve model onto to the 3D cardiac model to create a superimposed model; and displaying the superimposed model.

16. The method of claim 15, wherein displaying the superimposed model further comprises displaying a path model for implantation of the cardiovascular device within the heart of the patient.

17. The method of claim 12, wherein generating, by the at least a computing device, the at least a 3D cardiac model comprises:

extracting at least a cardiac feature from the at least an ultrasound image; and segmenting the at least an ultrasound image into a plurality of image segments as a function of the at least a cardiac feature.

18. The method of claim 12, wherein generating, by the at least a computing device, the at least a 3D cardiac model representative of the heart of the patient comprises:

receiving the generic 3D model; and generating the at least a 3D cardiac model using a statistical shape model.

19. The method of claim 18, wherein at least one anomaly of the one or more anomalies comprises a spatial distortion of at least one cardiac feature.

20. The method of claim 12, wherein receiving, by the at least a computing device, the at least valve model representative of the at least a cardiovascular device to be placed within the patient comprises:

generating a search query for a device database as a function of the valve model datum, wherein the device database comprises a plurality of valve models representative of a plurality of cardiovascular devices; and identifying at least one available valve model from the plurality of valve models as a function of the search query.

21. The method of claim 20, wherein the search query comprises an annulus diameter associated with the valve model.

22. The method of claim 12, wherein generating the at least a 3D cardiac model comprises generating the at least a 3D cardiac model using a point completion model.

* * * * *